United States Patent
Medoff

(10) Patent No.: US 11,202,665 B2
(45) Date of Patent: Dec. 21, 2021

(54) METHOD OF CHANGING A CONFIGURATION OF A BONE HAVING A LENGTH AND SYSTEM FOR FACILITATING CHANGING OF A CONFIGURATION OF A BONE

(71) Applicant: TriMed, Incorporated, Santa Clarita, CA (US)

(72) Inventor: Robert Medoff, Kailua, HI (US)

(73) Assignee: TriMed, Incorporated, Santa Clarita, CA (US)

( * ) Notice: Subject to any disclaimer, the term of this patent is extended or adjusted under 35 U.S.C. 154(b) by 206 days.

(21) Appl. No.: 16/460,777

(22) Filed: Jul. 2, 2019

(65) Prior Publication Data

US 2020/0008847 A1 Jan. 9, 2020

Related U.S. Application Data

(60) Provisional application No. 62/693,535, filed on Jul. 3, 2018.

(51) Int. Cl.
*A61B 17/56* (2006.01)
*A61B 17/58* (2006.01)
*A61B 17/80* (2006.01)
*A61F 2/30* (2006.01)
*A61B 17/68* (2006.01)

(52) U.S. Cl.
CPC .... *A61B 17/8019* (2013.01); *A61B 2017/564* (2013.01); *A61B 2017/681* (2013.01)

(58) Field of Classification Search
CPC combination set(s) only.
See application file for complete search history.

(56) References Cited

U.S. PATENT DOCUMENTS

2015/0051650 A1* 2/2015 Verstreken ............. A61B 17/80
606/281

\* cited by examiner

*Primary Examiner* — Sameh R Boles
(74) *Attorney, Agent, or Firm* — Wood, Phillips, Katz, Clark & Mortimer

(57) ABSTRACT

A method of changing a configuration of a bone by placing a bone plate and a spacing assembly in a cutting state wherein: a) the bone plate is connected to the bone and overlies a surface of the bone; and b) the spacing assembly cooperates between the bone plate and bone so as to maintain a gap region. A cutting instrument is used to cut into the bone towards the gap region and at least substantially through the bone between first and second bone portions. After cutting into the bone, the bone plate and spacing assembly are changed from the cutting state into a second state. An apparatus allows performance of the method.

25 Claims, 19 Drawing Sheets

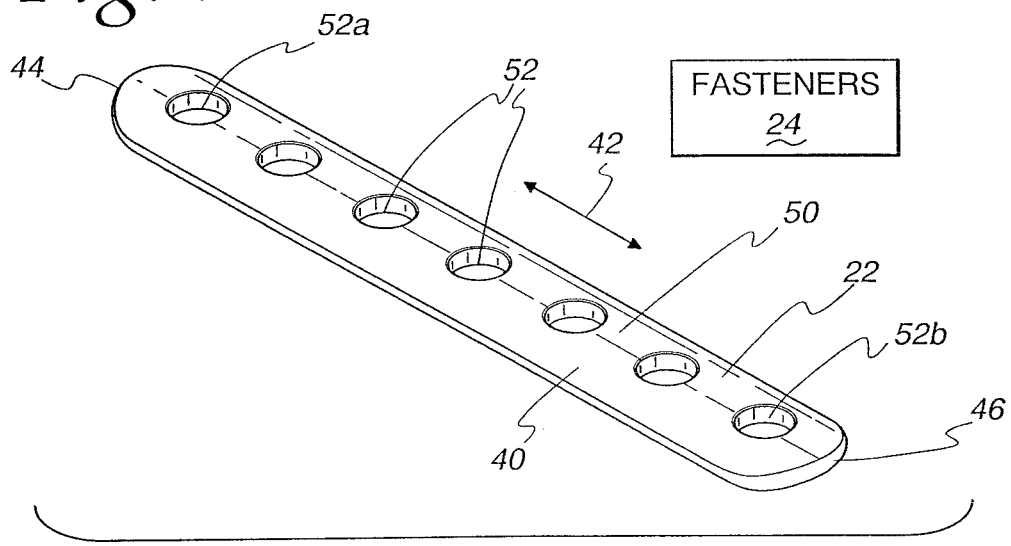
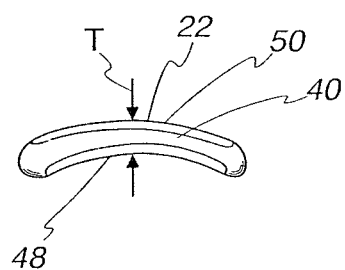
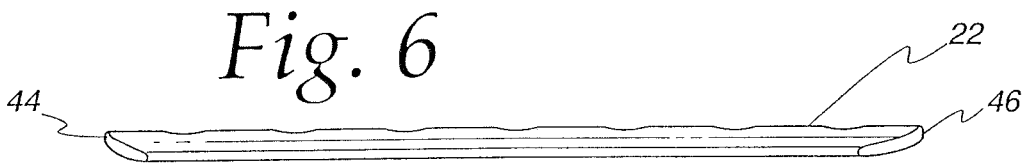
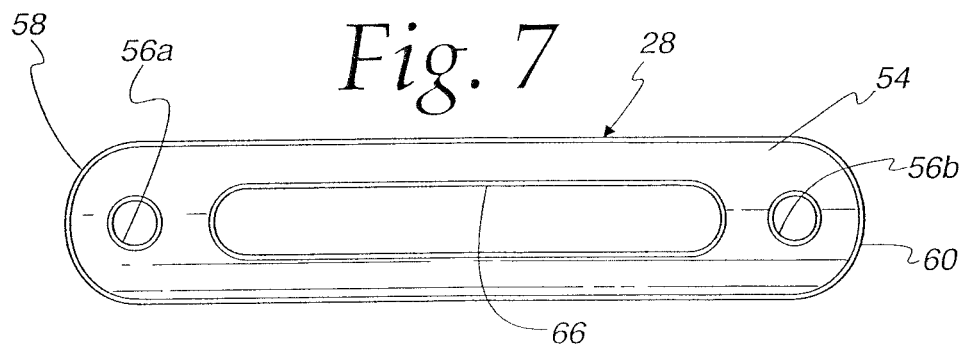

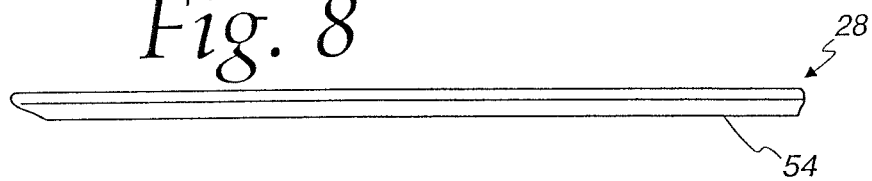
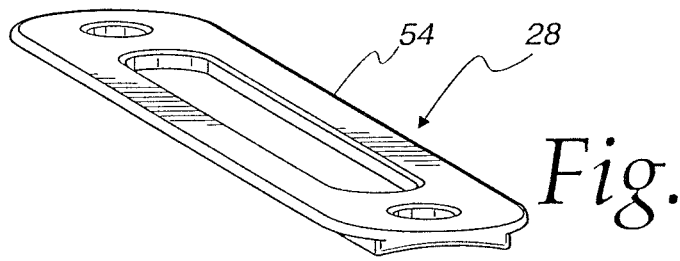
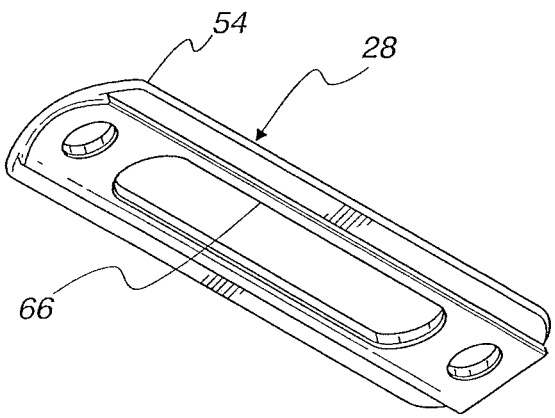
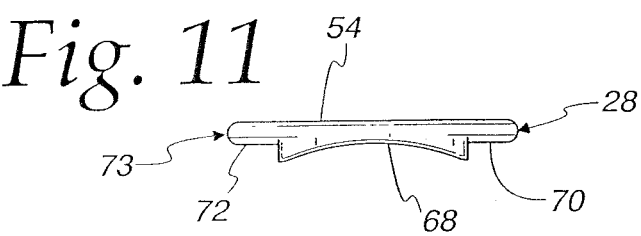
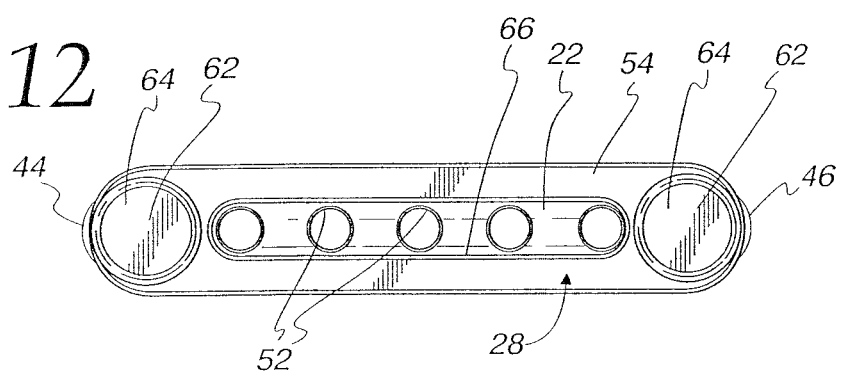

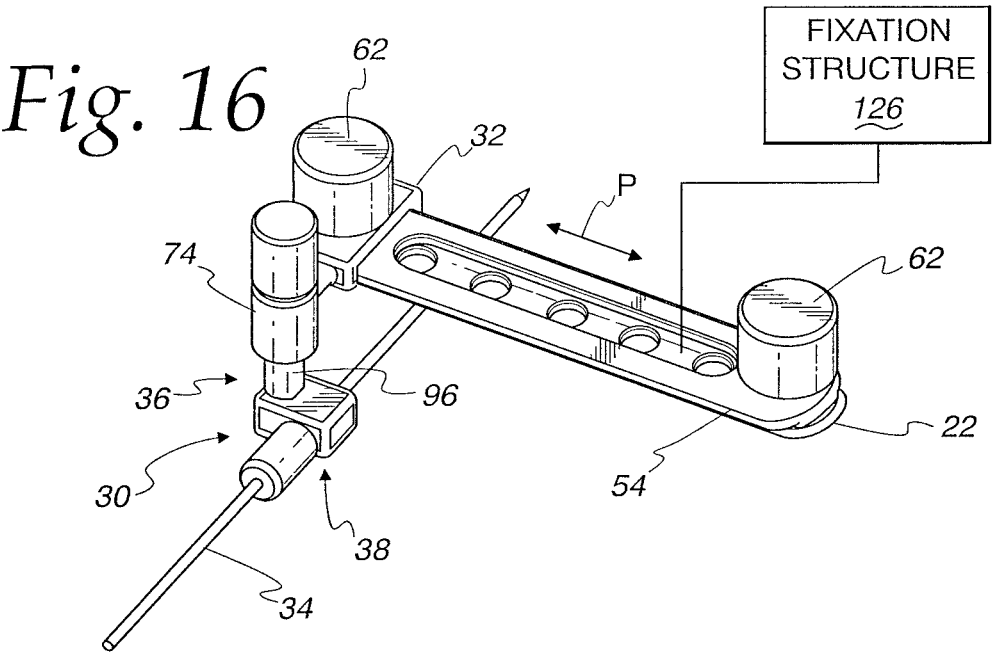
Fig. 16
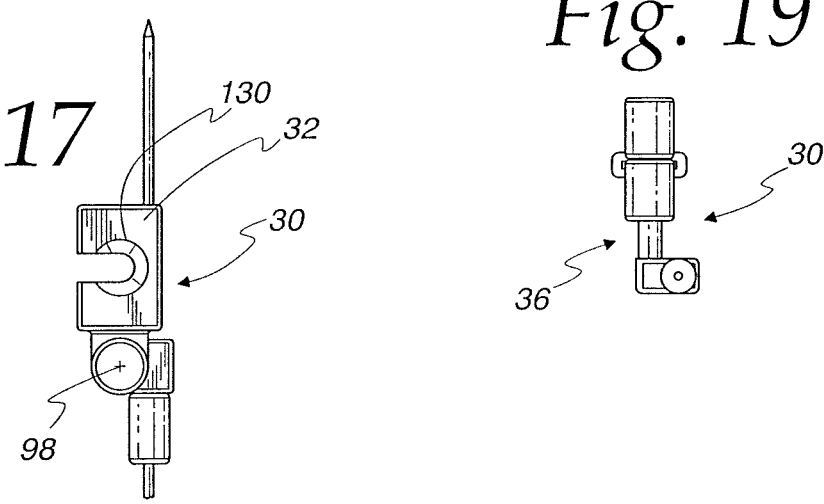
Fig. 17
Fig. 19
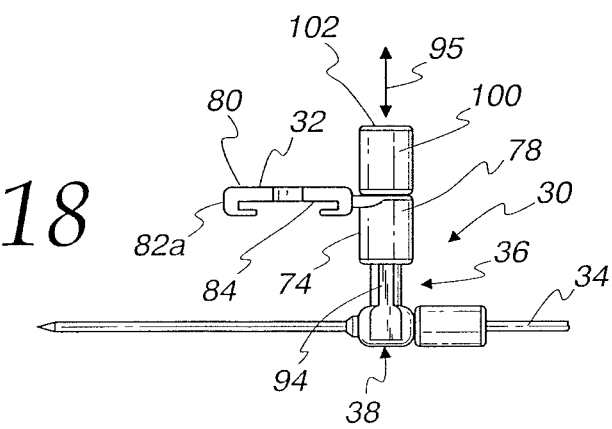
Fig. 18

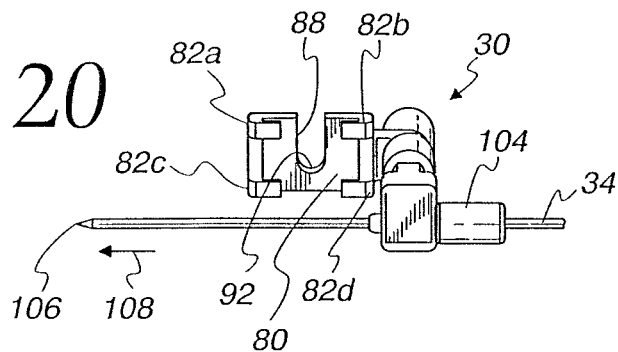
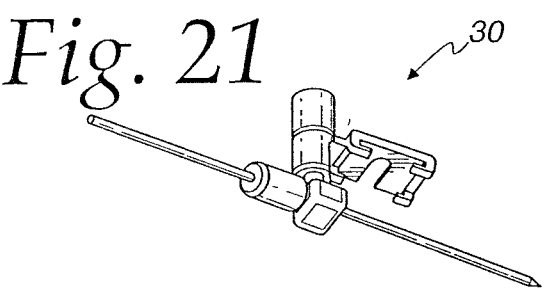
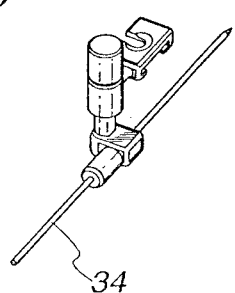
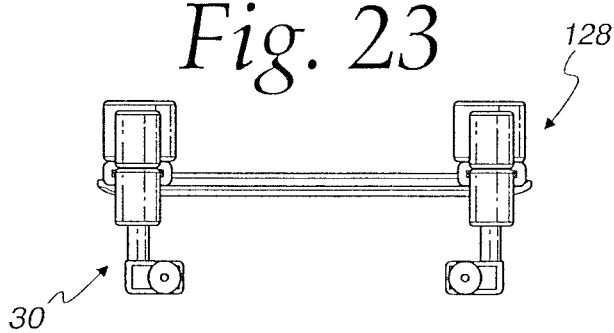
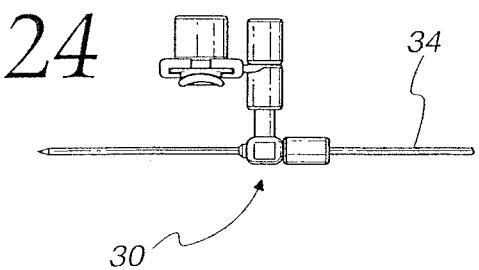

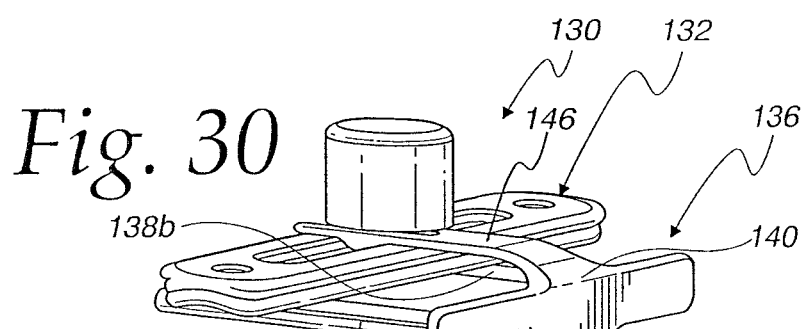
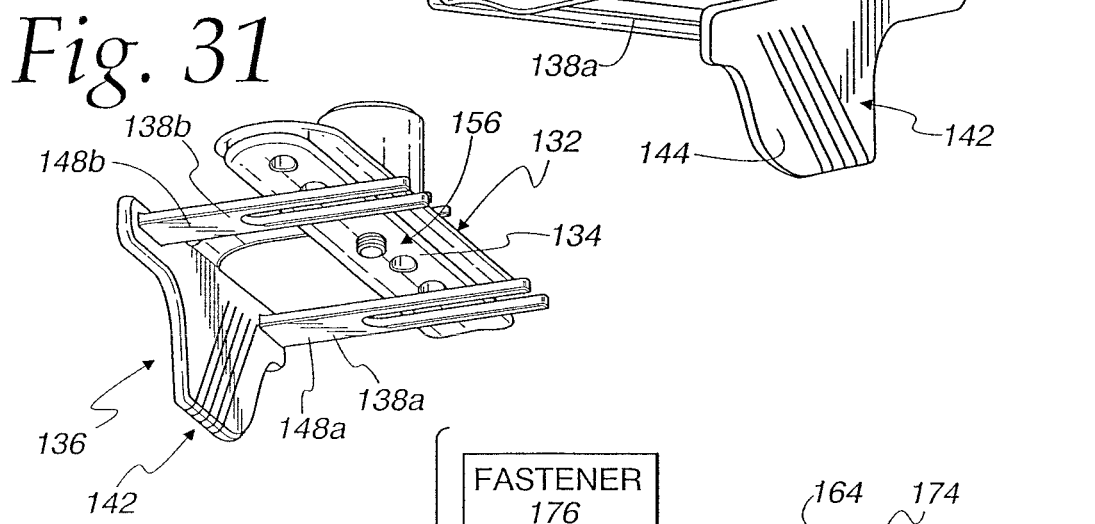
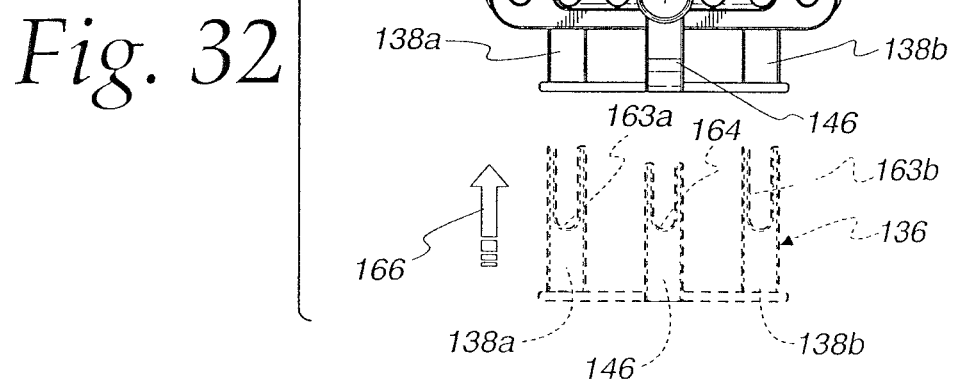
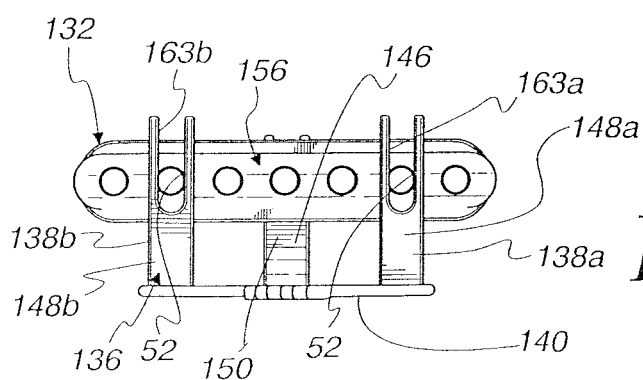

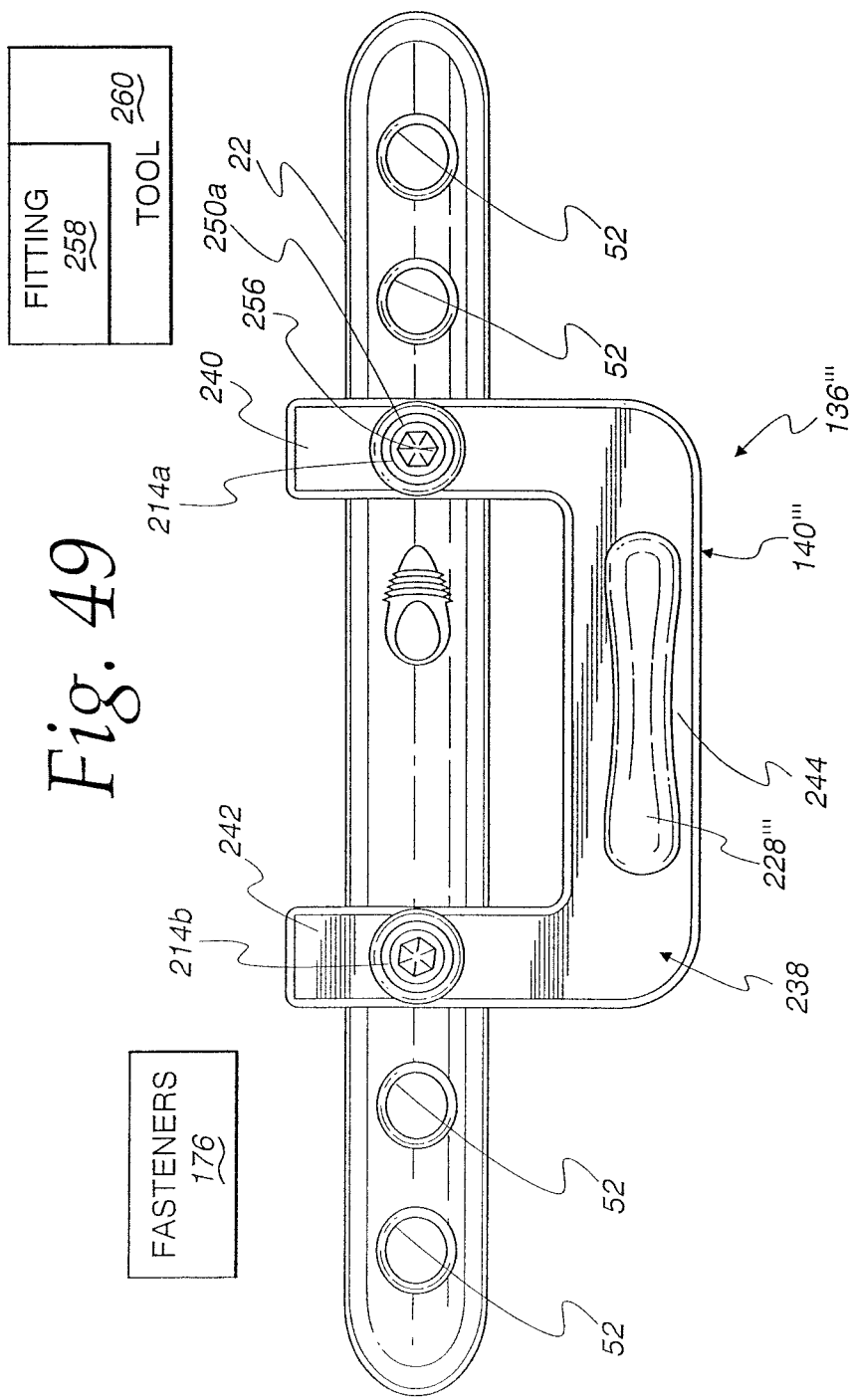

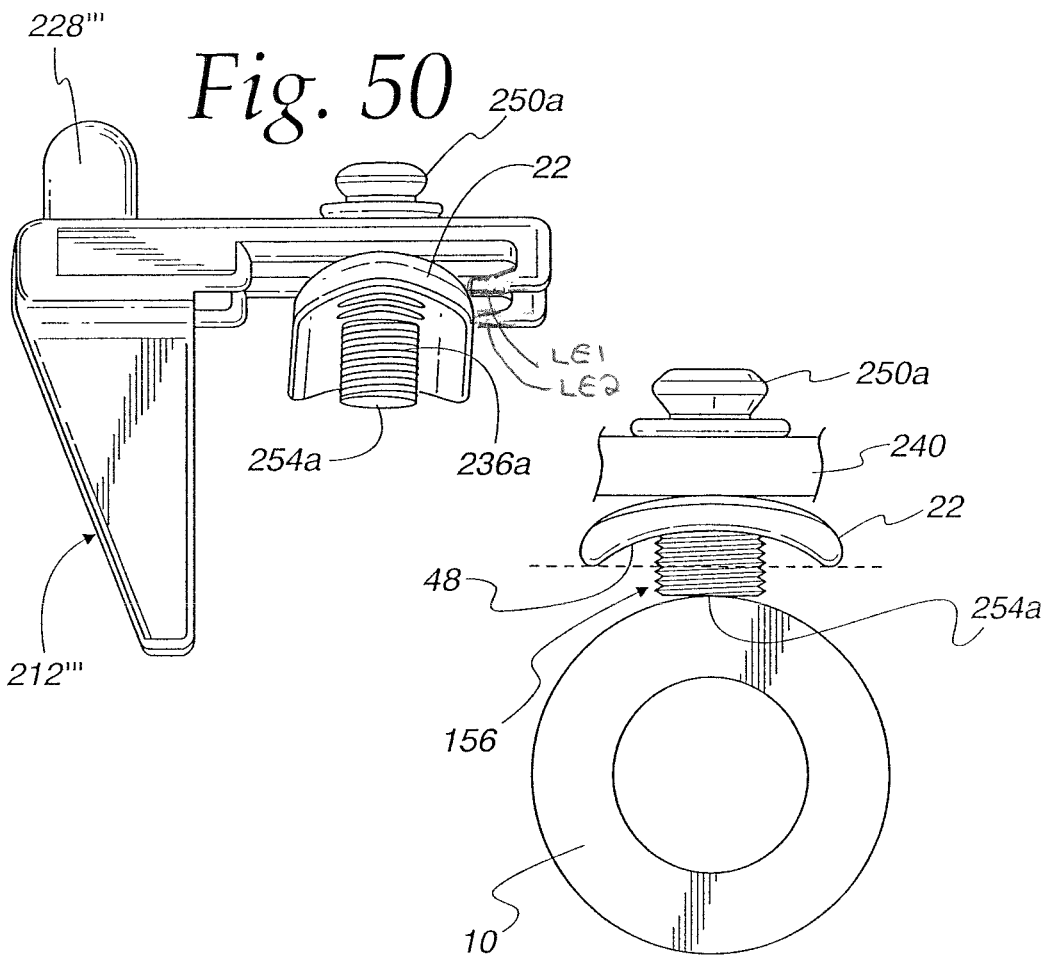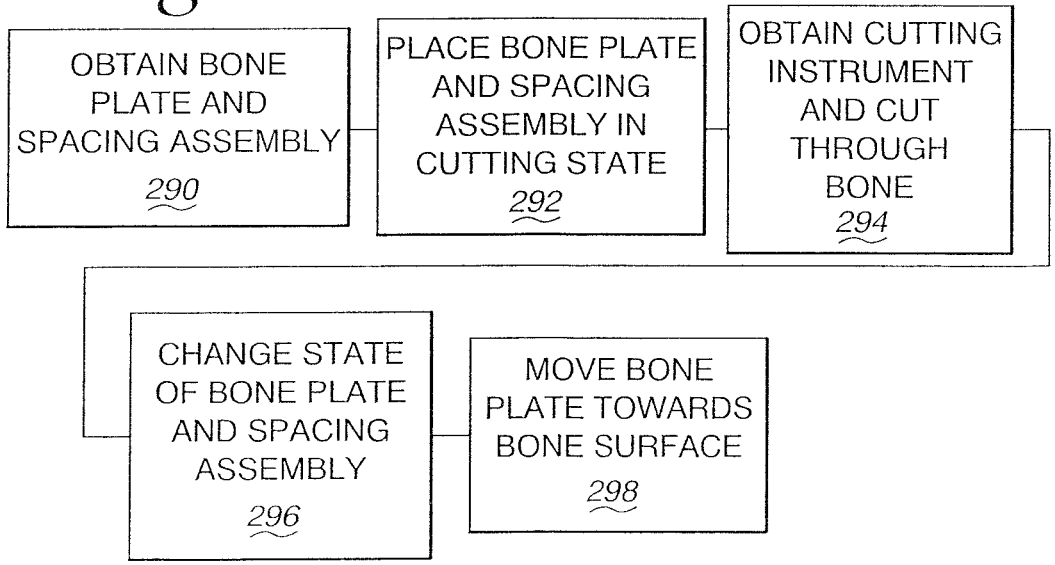

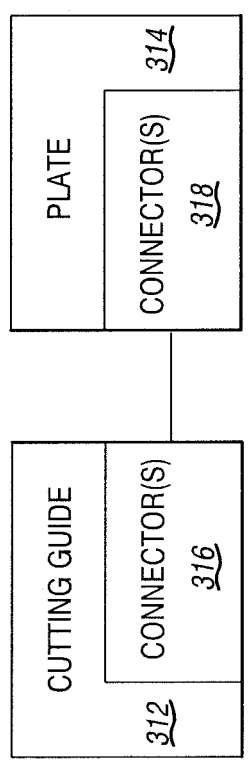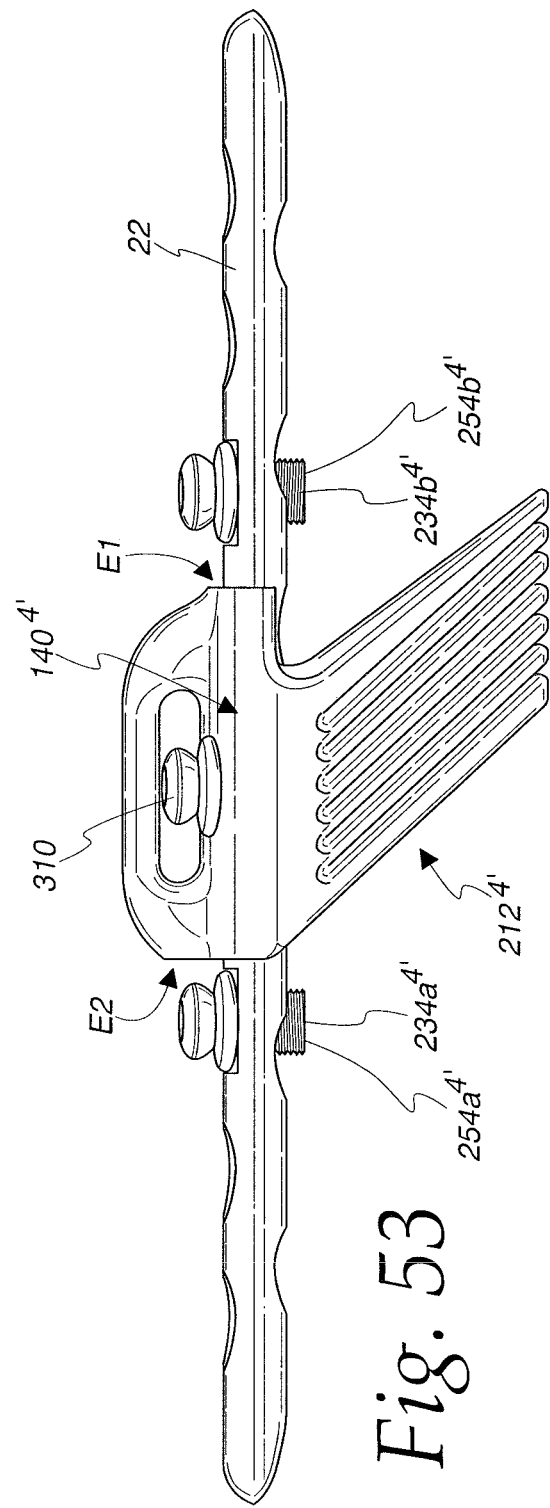

METHOD OF CHANGING A CONFIGURATION OF A BONE HAVING A LENGTH AND SYSTEM FOR FACILITATING CHANGING OF A CONFIGURATION OF A BONE

BACKGROUND OF THE INVENTION

Field of the Invention

This invention relates to surgical instrumentation and procedures and, more particularly, to a method and system relating to changing the configuration of a bone.

Background Art

Bone osteotomies (i.e., procedures involving cutting bone) are used to correct malalignment of osseous structures in the human skeleton. This procedure is commonly used to correct malalignment of rotation, translation, or excessive/inadequate length of the bone involved. When used to correct excessive or inadequate axial length of the bone, the procedure is categorized as a lengthening or shortening osteotomy. Osteotomies to gain or reduce length may be done in any bone; a common example in the upper extremity is called an ulnar shortening procedure. This procedure is done to correct excessive ulnar length causing the distal end of the bone to abut against the bones of the wrist. The prior art will be described hereinbelow with respect to an ulnar shortening procedure. The ulna is just representative of many different bones that have been similarly treated. Further, bone shortening, as described below, is likewise but a representative procedure that involves bone cutting.

The first description of ulnar shortening used a free hand technique where a segment of bone was simply cut transversely without a guide and the bones brought manually together and fixed. This required free hand precision to ensure that the cuts were exactly parallel, and created challenges in accurately aligning and fixing two highly unstable segments of bone by hand. Later modifications in the technique included making an oblique or step cut to provide at least some control of the unstable end and aid in precise alignment (particularly rotation) between the bone segments as they were apposed. However, these methods still require the surgeon to have a high level of skill and ability to create precisely cut surfaces that match perfectly, as well as ensure that bone ends are placed in accurate apposition and alignment. Uneven cuts or misjudging the size of the resected segment can be common, and result in non-unions, malunions, and/or inadequate or excessive correction of the deformity.

The Rayhack system was the first significant instrumentation system that employed a sequence of guides to try to improve the precision of cuts and simplify alignment and fixation of the bone ends for ulnar shortening osteotomies. With this system, the surgeon first attaches a saw guide to the bone with screws; this guide is then used to create precise, accurate oblique cuts to remove a predetermined length of bone and create parallel bone surfaces. The guide is then removed and a bone plate applied across the unstable segments. A compression block is then fixed with an extra-long screw on one side. A screw is placed into a slotted hole through the bone plate at the other end of the plate and compression clamp thumbscrews tightened to bring the two sides of the compression block together, shortening the bone by the sliding action of the screw in the sliding hole of the plate. Additional screws are placed into the plate and the first screws removed to remove the block and replaced with appropriate length screws.

Although this system was a significant advance in the technique of ulnar shortening and removed much of the imprecision and guesswork of freehand cuts and guiding the bone resection, it is cumbersome and complicated. For example, the technique brochure for this technique lists a total of fifteen separate steps in order to complete the procedure. Second, it requires that the guide is physically screwed into the bone, adding time to the procedure, and requires screws to be placed and removed multiple times into a single hole, which can compromise thread purchase. Yet another issue is the need for removal of the guide and then application of the plate, which requires the surgeon to deal with aligning two grossly unstable bone and freely moveable bone segments during the procedure. He/she still needs to provisionally hold the plate on these unstable pieces as fixation screws are placed. The plate requires a bone screw through a slotted hole; this bone screw is loosened and the shortening done by allowing the screw (which is attached to the bone) to slide within the slotted hole. The screw is then tightened—these steps of inserting, then loosening, then compressing through this loose screw, then re-tightening can adversely distort the threaded bone hole and compromise fixation by the screw.

TriMed, Inc., the assignee herein, developed another ulnar shortening system that improved on the Rayhack system to overcome some of the above issues. In this system, a plate is first secured on one side of the anticipated cut with three bone screws (the fixed segment), and a single screw at the end of a slotted hole is placed on the opposite side (what will become the sliding segment). The plate has two additional pin slots through which pins are placed to prevent angular movement of the sliding segment after a cut is made.

A saw guide is attached using two holes along the side of the plate and used to make the bone cuts (one at a time). At the center of the plate, the undersurface is undercut to allow full oscillation of a saw blade to ensure that the cut is completely through the bone surface that sits under the plate. Compression is accomplished by using an instrument that attaches to one of the holes along the edge of the fixed side of the plate and the bone on the sliding side with a transverse pin. The bone screw in the sliding hole of the plate and vertical anti-rotation pins guide the movement of the sliding segment to shorten the bone and precisely appose the surfaces to allow the surgeon to complete fixation.

Although a significant improvement on the Rayhack system in terms of simplicity, precision and reproducibility over a wide variation of surgeon experience and ability, the TriMed system still has some features that could be improved. Since the plate is applied before the cut is made (as opposed to the Rayhack system), the plate has a cutout at the center of its undersurface to allow complete movement of the saw blade to fully divide the bone at the edge under the plate. This feature, along with the need for the pin holes along the edge of the plate to allow attachment of the guide and compression instrument during the procedure, requires that the plate have at least a certain thickness in order to accommodate these features. This may make the plate thicker than desirable for bone fixation and may result in increased soft tissue prominence which can require later removal as well as cause stress shielding of the bone under the plate (that can lead to later fracture). In addition, the need for a slotted bone screw hole and pin slots to allow the shortening add to the overall plate length and require a relatively long incision of corresponding length in order to apply the plate. Furthermore, the need for slotted holes for the screws and pins results in a significant separation between the final bone screw in the slotted hole and the osteotomy site, which is not optimal for fixation (biomechanically better to have fixation screws spread out in each bone segment, starting relatively close to the osteotomy site). Finally, guiding the bone shortening by movement of bone fixation elements through slotted holes in the plate limits the maximal length of shortening to the length of the slots. The system also places a lag screw across the oblique osteotomy cut, and the specific design of the plate requires the direction of the cut and direction of the lag screw to be placed in a single orientation. As some surgeons prefer the cut direction and lag screw in the opposite direction than provided, the system may not meet their needs. Because of the nature of the design which requires multiple screws on either side of the cut, the system is best suited to osteotomies in the center of a long bone, as opposed to osteotomies at the end of the bone where only a short segment on one side is available.

Variations in the basic TriMed-style plate have been made that include minor changes and improvements to the implant shortening system.

The challenge of allowing cutting fully through a bone without interference from a bone plate, and/or any other component used to assist the performance of bone osteotomies, persists to this day. As a result, surgeons have generally been required to either: a) use thicker bone plates, as described above, that may be configured to produce a discrete gap region for a cutting component to enter; or b) try and carefully maneuver a cutting component fully through a bone so that it does not impinge upon the bone plate or other structure used to assist the performance of an osteotomy. The former approach requires use of an undesirably thick bone plate, which has drawbacks as described above, whereas the latter requires highly skilled and careful maneuvering of a cutting instrument, which may complicate and lengthen the performance period, for a particular procedure.

The industry continues to work on different systems and techniques that address one or more of the above areas.

SUMMARY OF THE INVENTION

In form, the invention is directed to a method of changing a configuration of a bone having a length. The method includes the steps of: obtaining a bone plate; obtaining a spacing assembly; placing the bone plate and spacing assembly in a cutting state wherein: a) the bone plate is connected to the bone and overlies a surface of the bone; and b) the spacing assembly cooperates between the bone plate and bone so as to maintain a gap region between at least a part of the bone plate and the bone surface which the bone plate overlies; obtaining a cutting instrument with a cutting component; with the bone plate and spacing assembly in the cutting state, using the cutting component on the cutting instrument to cut into the bone towards the gap region and at least substantially through the bone between first and second bone portions; and, after cutting into the bone, changing the bone plate and spacing assembly from the cutting state into a second state wherein the at least part of the bone plate can be moved towards the surface of the bone to be closer to the surface of the bone than is possible with the bone plate and spacing assembly in the cutting state.

In one form, the method further includes the step of moving the at least part of the bone plate towards the bone surface after cutting into the bone to thereby place the bone plate in an operative position on the bone.

In one form, the method further includes the step of securing the bone plate in the operative position with the bone plate spanning the first and second bone portions.

In one form, the bone plate has at least one through opening. At least one fastener is directed through the at least one through opening and into the bone. The step of securing the bone plate includes tightening the at least one fastener.

In one form, with the bone plate and spacing assembly in the cutting state, a cutting guide is used that is configured to guide movement of the cutting instrument and/or the cutting component on the cutting instrument in at least one controlled path to thereby strategically cut into the bone between the first and second bone sections.

In one form, the spacing assembly is configured to maintain the gap region through spacer parts that act between the bone and bone plate at first and second spaced locations.

In one form, the bone plate has a length. The first and second locations are spaced lengthwise of the bone plate. The bone is cut at a location between the first and second locations.

In one form, the cutting guide has a first elongate slot to guide movement of the cutting instrument and/or the cutting component in the one controlled path.

In one form, the cutting guide has a second elongate slot to guide movement of the cutting instrument and/or the cutting component in a second controlled path.

In one form, the spacing assembly is configured to maintain the gap region through spacer parts that act between the bone and bone plate at first and second spaced locations. The spacing assembly has a frame that moves as one piece. The frame defines the spacer parts and the cutting guide.

In one form, the frame has one piece that defines the spacer parts and at least a part of the cutting guide.

In one form, the step of changing the bone plate and spacing assembly from the cutting state into the second state involves translating the frame relative to the bone plate from a starting position, spaced from the bone plate, into an operative position.

In one form, the method further includes the step of releasably fixing the frame relative to the bone plate to thereby maintain the bone plate and spacing assembly in the cutting state.

In one form, the step of releasably fixing the frame includes directing a fastener relative to the frame and into the bone plate.

In one form, the method further includes the step of captively engaging the bone plate between spaced surfaces on the spacing assembly.

In one form, the bone plate has a length. With the bone plate and spacing assembly in the cutting state, the gap region is defined over substantially an entire bone plate length.

In one form, the gap region has a dimension of 1-3 mm between the bone plate and bone surface.

In one form, the method further includes the step of urging the bone plate towards the bone surface with the bone plate and spacing assembly in the cutting state before cutting through the bone.

In one form, the step of urging the bone plate towards the bone surface includes exerting a force on the bone plate at two spaced locations between which the bone is cut.

In one form, the force is exerted at each of the two spaced locations through a fastener extending through the bone plate and into the bone.

In one form, the spacing assembly has a frame and at least one setting component with a free end. The step of placing the bone plate and spacing assembly in the cutting state involves advancing the at least one setting component relative to the frame and bone plate so as to bear the free end of the at least one setting component against the bone surface without appreciably penetrating the bone surface to thereby maintain at least a part of the gap region.

In one form, the step of changing the bone plate and spacing assembly from the cutting state into the second state involves separating at least a part of the spacing assembly from the bone and the bone plate.

In one form, with the bone plate and spacing assembly in the cutting state, at least a part of the bone plate directly overlies the bone surface.

In one form, the step of urging the bone plate towards the bone surface causes a part of the spacing assembly to be compressibly captively held between the bone plate and the bone surface.

In one form, the cutting guide is separate from the spacing assembly.

In one form, the invention is directed to a system for facilitating changing of a configuration of a bone having a length. The system includes: a bone plate having a surface to overlie a surface of a bone to which the bone plate is to be fixed in an operative position; and a spacing assembly. The spacing assembly is configured to be placed together with the bone plate selectively in: a) a cutting state wherein the spacing assembly maintains a gap region between at least a part of the bone plate surface and a bone surface which the bone plate surface is situated to overlie; and b) a second state wherein the at least part of the bone plate surface can be moved closer to a bone surface, that the bone plate surface overlies with the bone plate in the operative position, than with the bone plate and spacing assembly in the cutting state. A cutting component can be directed fully through a bone and into the gap region with the spacing assembly and bone plate in the cutting state. After the bone is cut, the bone plate and spacing assembly can be changed into the second state whereupon the bone plate can be placed in the operative position.

In one form, the system further includes a cutting guide configured to guide movement of a cutting instrument and/or a cutting component on the cutting instrument to cut through a bone that is being treated with the bone plate and spacing assembly in the cutting state.

In one form, the system has a frame that moves as one piece. The frame defines at least part of the cutting guide and at least one spacer part on the spacing assembly that maintains the gap region.

In one form, the frame has first and second spacer parts that maintain the gap region at spaced locations.

In one form, the cutting guide has a first elongate slot to guide movement of a cutting instrument and/or a cutting component on a cutting instrument in a first controlled path.

In one form, the cutting guide has a second elongate slot to guide movement of a cutting instrument and/or a cutting component on a cutting instrument in a second controlled path.

In one form, the frame has a wall on which the cutting guide is provided. The one spacer part projects in cantilever fashion from the wall.

In one form, the spacing assembly has a frame with a wall. At least one spacer part projects in cantilever fashion from the wall. The at least one spacer part resides between the bone plate and bone surface on the bone with the bone plate and spacing assembly in the cutting state.

In one form, the frame has an arm projecting from the wall. The bone plate resides between the arm and the at least one spacer part with the bone plate and spacing assembly in the cutting state.

In one form, the spacing assembly further includes an adjustable setting component. The adjustable setting component is advanced from the arm to against the bone plate to thereby bear the bone plate against the at least one spacer part with the bone plate and spacing assembly in the cutting state.

In one form, the bone plate has a length. The at least one spacer part consists of first and second spacer parts spaced lengthwise of the bone plate with the spacing assembly and bone plate in the cutting state. The arm resides between the first and second spacer parts along the length of the bone plate with the spacing assembly and bone plate in the cutting state.

In one form, the wall has a discrete tab that projects in cantilever fashion on the wall. The tab is configured to be grasped between a user's fingers to facilitate handling of the spacing assembly.

In one form, the spacing assembly has a frame and a first setting component with a free end. The first setting component projects from the frame through the bone plate so that the free end can bear against the bone surface without appreciably penetrating the bone surface to maintain at least a part of the gap region with the bone plate and spacing assembly in the cutting state.

In one form, the spacing assembly has a second setting component that functions in the same manner as the first setting component.

In one form, the frame has a U-shaped portion that overlies the bone plate with the bone plate and spacing assembly in the cutting state.

In one form, the setting components each has a threaded body and an enlarged head that can be grasped and turned to thereby control extension of the free ends of the setting components beyond the bone plate and thereby a dimension of the gap region.

In one form, the "U" shape is defined by two spaced legs and a base portion connecting the two spaced legs. The setting components project one each from the two spaced legs.

In one form, the frame has a discrete tab projecting from the base portion that is configured to be grasped between a user's fingers to facilitate handling of the spacing assembly.

In one form, the system further includes a cutting guide on the frame configured to guide movement of a cutting instrument and/or a cutting component on the cutting instrument to thereby cut through a bone that is being treated with the bone plate and spacing assembly in the cutting state.

In one form, at least a part of the cutting guide is formed as one piece with a part of the frame.

In one form, the cutting guide projects in cantilever fashion on the frame.

BRIEF DESCRIPTION OF THE DRAWINGS

FIG. 4 is a perspective view of one form of bone plate, as shown schematically in FIG. 2;

FIG. 5 is an end elevation view of the bone plate in FIG. 4;

FIG. 6 is a side elevation view of the bone plate in FIGS. 4 and 5;

FIG. 7 is a plan view of an elongate plate making up the guide assembly on the system in FIG. 2;

FIG. 8 is a side elevation view of the plate in FIG. 7;

FIG. 9 is a perspective view of the plate in FIGS. 7 and 8;

FIG. 10 is a view as in FIG. 9 but from a different perspective;

FIG. 11 is an end elevation view of the plate in FIGS. 7-10;

FIG. 12 is a plan view showing the bone plate in FIGS. 4-6 and plate in FIGS. 7-11 operatively connected;

FIG. 16 is a perspective view of the components in FIGS. 12-15 together with one form of bone part moving assembly as shown schematically in FIG. 2;

FIG. 17 is a plan view of the bone part moving assembly in FIG. 16;

FIG. 18 is an end elevation view of the bone part moving assembly in FIGS. 16 and 17;

FIG. 19 is a side elevation view of the bone part moving assembly in FIGS. 16-18;

FIGS. 20-22 are different perspective views of the bone part moving assembly in FIGS. 16-19;

FIG. 23 is a side elevation view of the components as in FIG. 16 and additionally including a bone attachment assembly, according to the invention;

FIG. 24 is an end elevation view of the components in FIG. 23;

FIG. 30 is a perspective view of one form of system, as shown schematically in FIG. 29, and with the bone plate and spacing assembly in a cutting state;

FIG. 31 is a view as in FIG. 30 from a different perspective;

FIG. 32 is a top view of the system in FIGS. 30 and 31;

FIG. 33 is a bottom view of the system in FIGS. 30-32;

and

Figure 42:
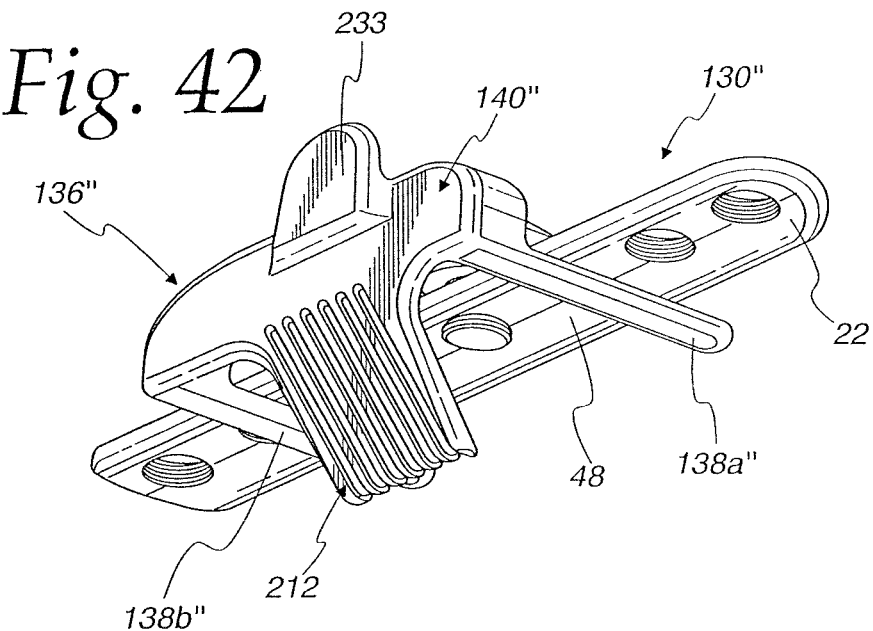
Figure 43:
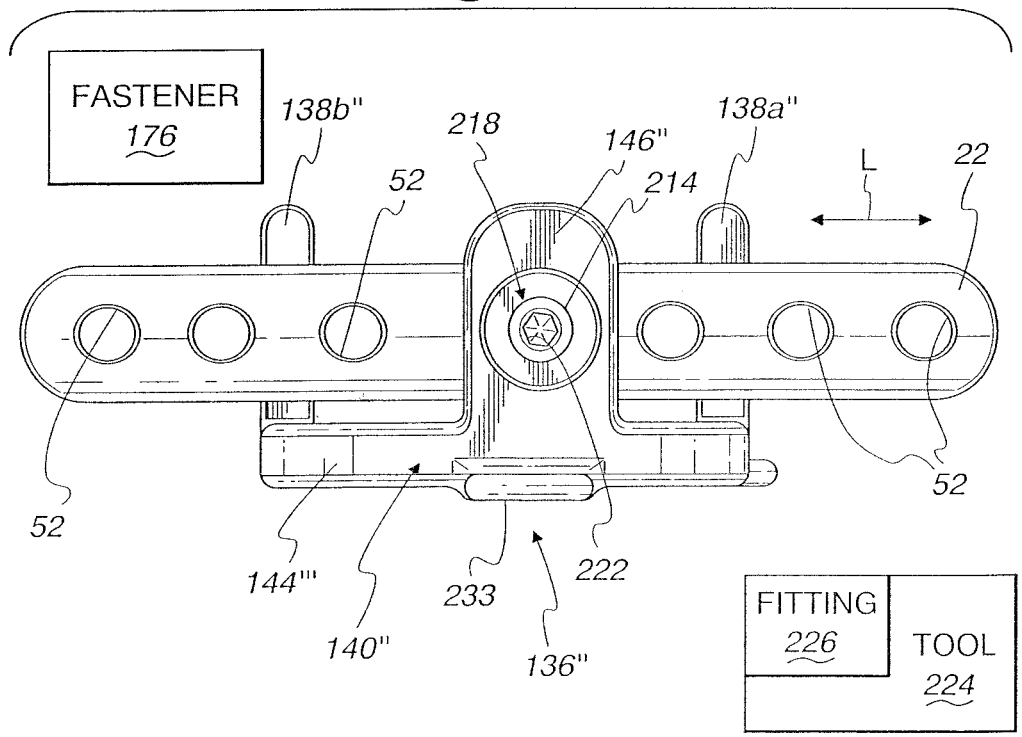
Figure 44:
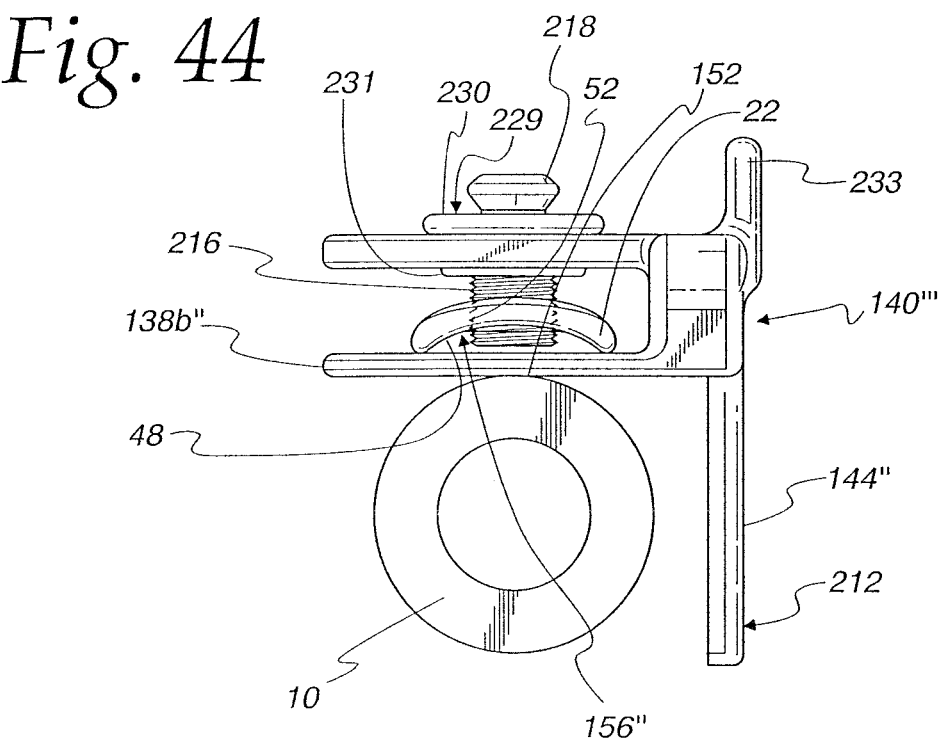
Figure 45:
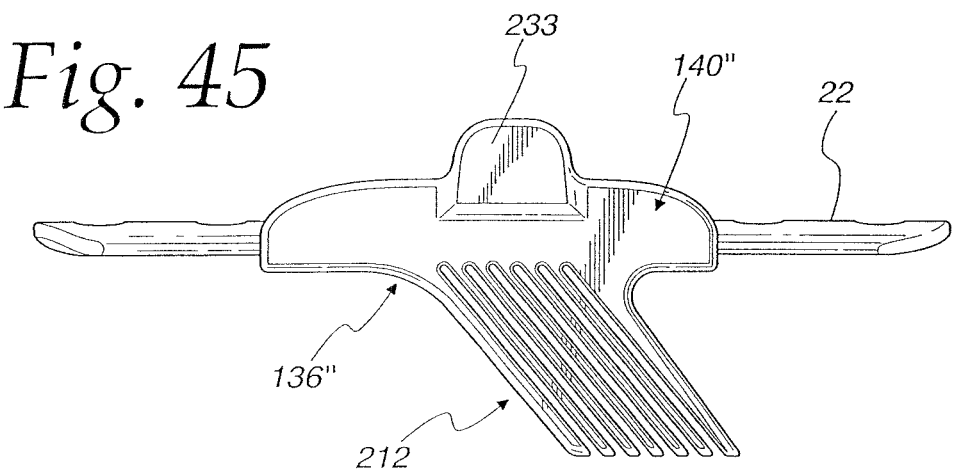
Figure 46:
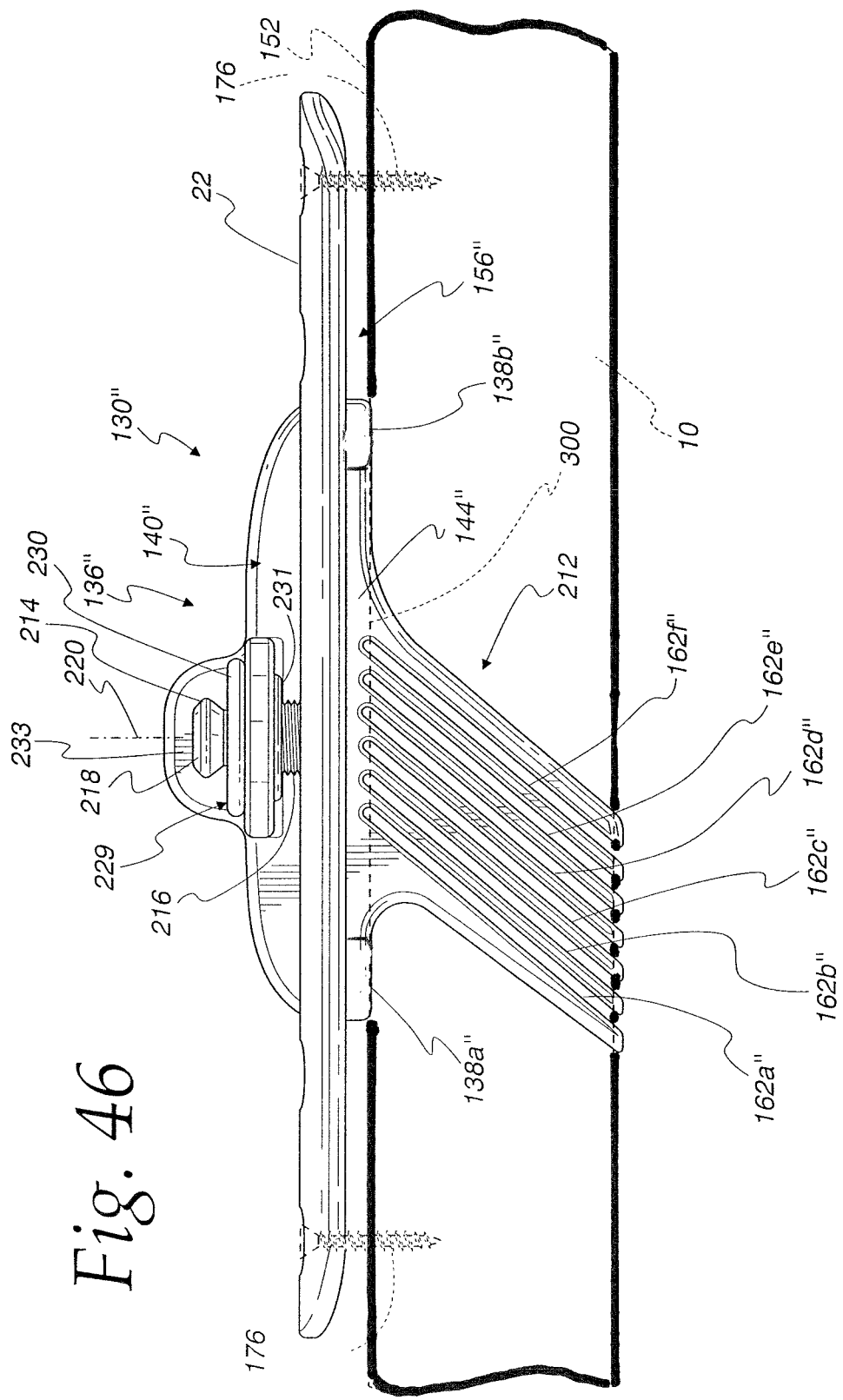
Figure 47:
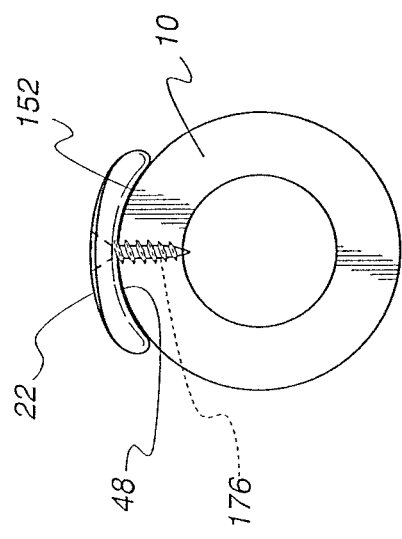
Figure 48:
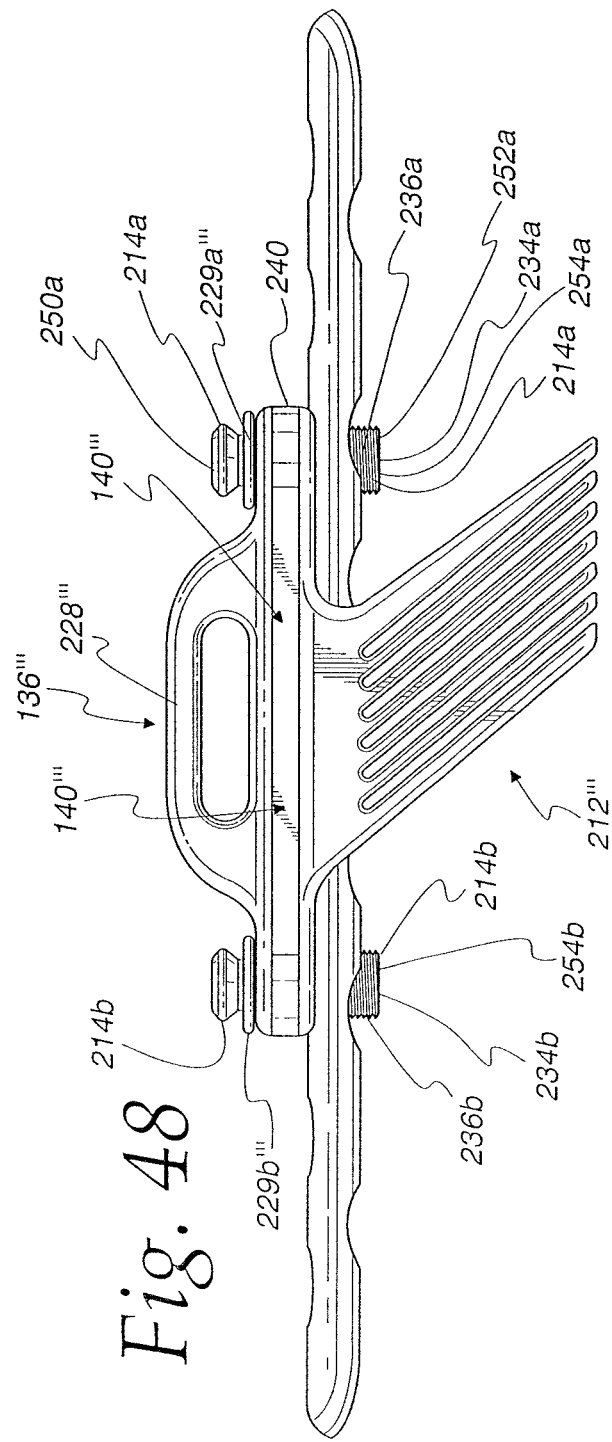

FIG. 42 is a perspective view of another form of system for changing a configuration of a bone, according to the invention, and including another form of spacing assembly and bone plate in a cutting state;

FIG. 43 is a plan view of the system in FIG. 42;

FIG. 44 is an end elevation view of the system in FIGS. 42 and 43 and in relationship to a bone;

FIG. 45 is a side elevation view of the system in FIGS. 42-44;

FIG. 46 is a view as in FIG. 45 from the opposite side;

FIG. 47 is an end elevation view of a bone with the bone plate in FIGS. 41-46 in its operative position;

FIG. 48 is a side elevation of another form of system, according to the invention, including another form of spacing assembly and bone plate in a cutting state;

FIG. 49 is a plan view of the system in FIG. 48;

FIG. 50 is a bottom perspective view of the system in FIGS. 48 and 49;

FIG. 51 is an end elevation view of the system in FIGS. 48-50 with the spacing assembly and bone plate in a cutting state on a bone;

FIG. 52 is a flow diagram representation of a method of changing a configuration of a bone according to the invention;

FIG. 53 is a view as in FIG. 48 showing a further modified form of system, according to the invention; and FIG. 54 is a schematic representation of a cutting guide and plate, according to the invention, with cooperating connectors that maintain the cutting guide and plate in operative relationship.

DETAILED DESCRIPTION OF THE PREFERRED EMBODIMENT

The present invention relates to both a method and system for changing the configuration of a bone. While prior art is described above in relationship to an ulnar osteotomy, the invention relates generically to any bone that is commonly reconfigured as through the performance of an osteotomy. Further, while the invention will be described with respect to an osteotomy involving shortening of a bone, the invention is not so limited and the structure and steps described herein are equally applicable and adaptable to other procedures, including but not limited to, lengthening.

Figure 1:
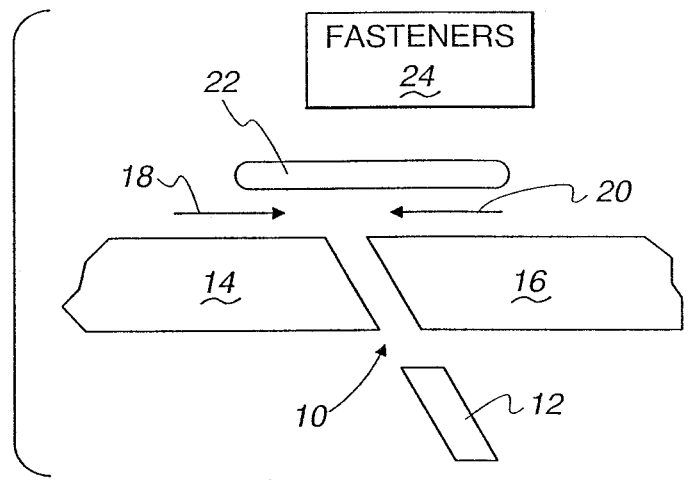
FIG. 1 is a schematic representation of a bone that has been cut to remove a fragment thereof and in relationship to a bone plate securable to separated bone portions by fasteners.

The invention will be described with respect to a bone 10, as shown schematically in FIG. 1, that is cut strategically to remove a bone fragment 12. This produces first and second bone sections 14, 16 that are thereafter urged against each other, as indicated by the arrows 18, 20. In the desired end relationship, the bone sections 14, 16 are held together by a spanning bone plate 22 fixed to the bone sections 14, 16 by appropriate fasteners 24. Individual fasteners may be directed through the bone plate 22 into one of the bone sections 14, 16 and/or into both bone sections 14, 16.

The focus initially will not be on the details concerning cutting of the bone 10, but rather repositioning and fixation of the bone sections 14, 16 after cutting, regardless of how that cutting is performed. Bone section repositioning and fixation are accomplished using the inventive system, as shown schematically at 26 in FIG. 2.

The system 26 consists of the aforementioned bone plate 22, a guide assembly 28 on the bone plate 22, and a bone part moving assembly 30. The guide assembly 28 and bone part moving assembly 30 are configured so that a part 32 of the bone part moving assembly 30 is guided in a controlled path along the length of the bone plate 22.

The system additionally includes a fixation element 34.

The bone part moving assembly 30 further includes a fixation element support 36 with a fixation element mount 38 configured to support the fixation element 34 and allow the support and fixation element 34 to be directed into bone without passing through the bone plate 22. Through this arrangement, the fixation element 34 is caused to move with the part 32 of the bone part moving assembly 30 together with a bone region into which the fixation element 34 is directed.

With this construction, with a first part of the bone plate 22 fixed to one bone portion, another bone portion movable relative to the one bone portion, and into which the fixation element is directed, can be moved as by manipulating the bone part moving assembly, guidingly toward the one bone portion by following movement of the part 32 of the bone part moving assembly 30 in its controlled path.

Figure 2:
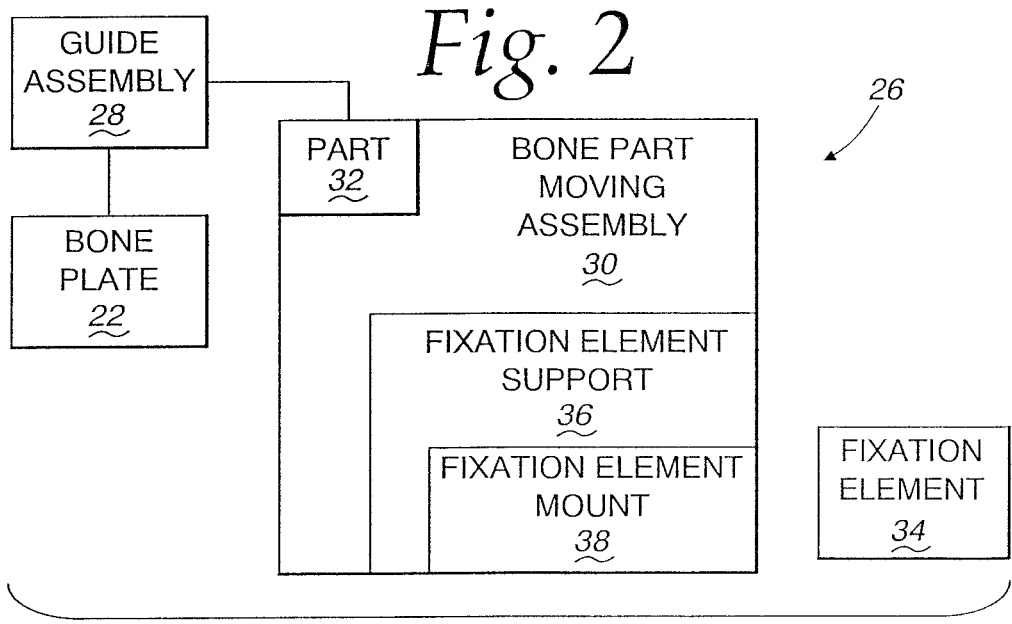
FIG. 2 is a schematic representation of a system for changing a configuration of a bone, according to the invention.
Figure 3:
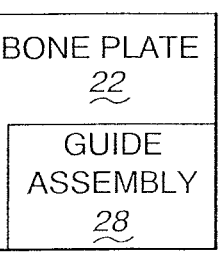
FIG. 3 is a schematic representation of an alternative form of bone plate and guide assembly on the system in FIG. 2.
Figure 13:
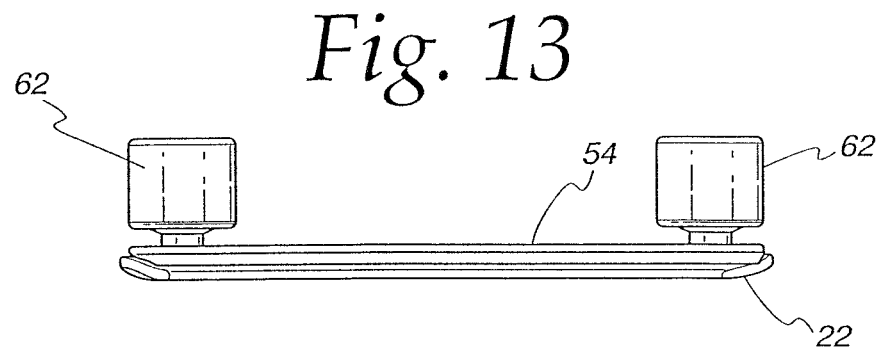
FIG. 13 is a side elevation view of the components in FIG. 12.

As shown in FIG. 3, the guide assembly 28 may be integrally formed with the bone plate 22 as opposed to being separate from, and attached to, the bone plate 22, as shown in FIG. 2.

The schematic representation of the system 26 is intended to encompass the specific forms thereof described hereinbelow, as well as virtually an unlimited number of variations of the components thereof and their interaction. Exemplary forms of the components, identified above, will now be described with respect to FIGS. 4-27, with it being understood that these specific forms are exemplary in nature only.

A specific form of the bone plate 22 is shown in FIGS. 4-6. The bone plate 22 has a body 40 with a length, as indicated by the double-headed arrow 42, between opposite ends 44, 46.

The body 40 has oppositely facing surfaces 48, 50, with the former curved to at least nominally match the contour of the region of the bone 10 which it overlies and to which it is fixed. The oppositely facing surface 50 has a complementary curvature so as to define a substantially uniform thickness T between the surfaces 48, 50 over the full width of the bone plate 22.

A plurality of through openings 52 are provided to accommodate the fasteners 24.

In this embodiment, the guide assembly 28 consists of at least an elongate plate, as shown at 54, in FIGS. 7-11. The elongate plate 54 is shown attached to the bone plate 22 in FIGS. 12-15.

Figure 14:
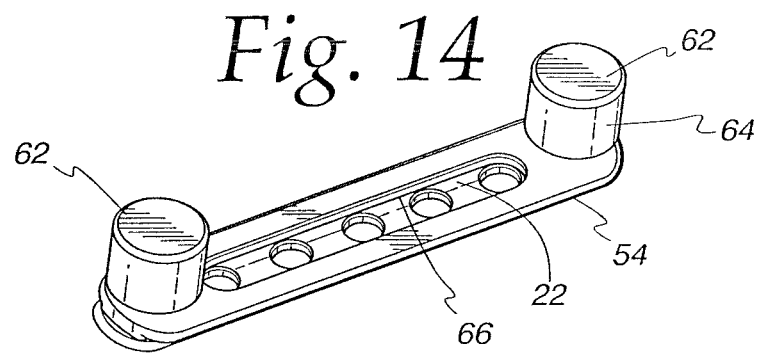
FIG. 14 is a perspective view of the components in FIGS. 12 and 13.

The perimeter shape of the elongate plate 54 is nominally matched to the perimeter shape of the bone plate 22, as viewed in plan, as seen most clearly in FIGS. 12 and 14. The elongate plate 54 extends preferably over at least a majority of the length of the bone plate 22. As depicted, the elongate plate 54 extends substantially fully between the spaced ends 44, 46 of the bone plate 22.

In this embodiment, the bone plate 22 has seven through openings, equidistantly spaced along the length of the bone plate 22, with endmost through openings 52a, 52b respectively adjacent the ends 44, 46 of the bone plate body 40.

The elongate plate 54 has discrete openings 56a, 56b respectively adjacent its lengthwise ends 58, 60, with the openings 56a, 56b respectively registrable with the bone plate openings 52a, 52b. Threaded fasteners 62 are directed through the aligned openings 52a, 56a; 52b; 56b to secure the elongate plate 54 fixedly to the bone plate 22. The fasteners 62 have enlarged heads 64 that can be conveniently grasped to allow a substantial torque to be applied without tools to tighten and release the fasteners 62.

The elongate plate 54 has an elongate opening 66 therethrough extending over a majority of the length of the bone plate 54. With this arrangement, a plurality, and in this case five, of the through openings 52 on the bone plate 22 register with the elongate opening 66, whereby appropriate fasteners can be strategically directed through the elongate opening 66 and the bone plate openings 52 and into bone.

The elongate plate 54 has a surface 68 that is curved to conform to the surface 50 of the bone plate 22 that it overlies. With this complementary surface arrangement, the connection of the elongate plate 54 to the bone plate 22 is stabilized.

The elongate plate 54 has oppositely projecting flanges 70, 72 that cooperatively define a guide rail 73 that makes up the guide assembly 28 for the part 32 of the bone part moving assembly 30.

Further details of the exemplary guide assembly 28 and bone part moving assembly 30 are shown in FIGS. 16-27.

The bone part moving assembly 30 consists of a frame 74. The frame 74 has a cylindrical body 78 from which the part 32 projects in cantilever fashion. The part 32 has a generally squared shape with a flat wall 80 with four depending legs 82a, 82b, 82c, 82d that are return bent to cooperatively define a T-shaped slot 84, in conjunction with the flat wall 80, as seen from the FIG. 18 perspective.

The slot 84 is configured to slidably receive the rail 73 defined cooperatively by the flanges 70, 72, This is a captive rail arrangement in which relative movement between the rail 73 and frame part 32 is confined to translational movement parallel to the lengths of the bone plate 22 and elongate plate 54. Accordingly, as seen in FIG. 16, the part 32 is guided by the rail 73 in the aforementioned controlled path, as indicated by the double-headed arrow P. Accordingly, precise controlled relative movement of bone portions can be effected in a linear path.

Figure 15:
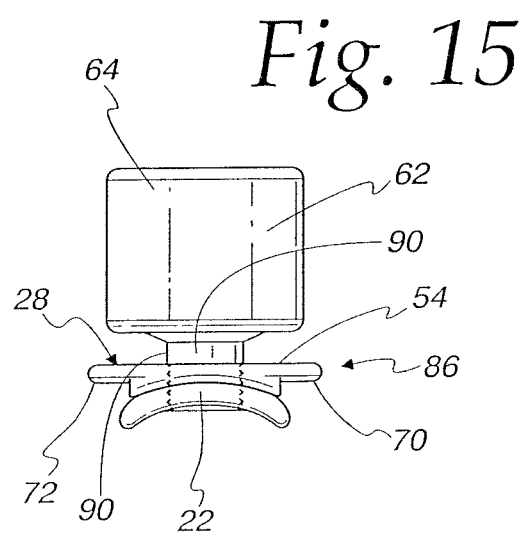
FIG. 15 is an end elevation view of the components in FIGS. 12-14.
Figure 25:
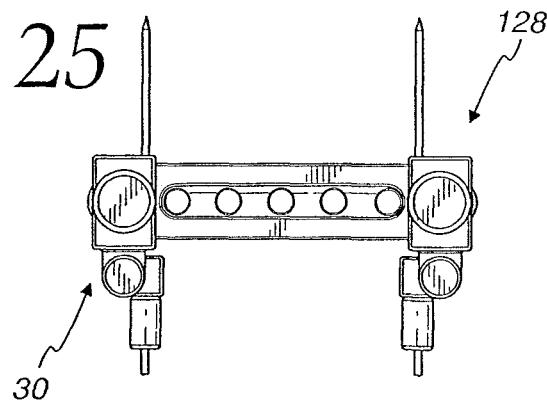
FIG. 25 is a plan view of the components in FIGS. 23 and 24.
Figure 26:
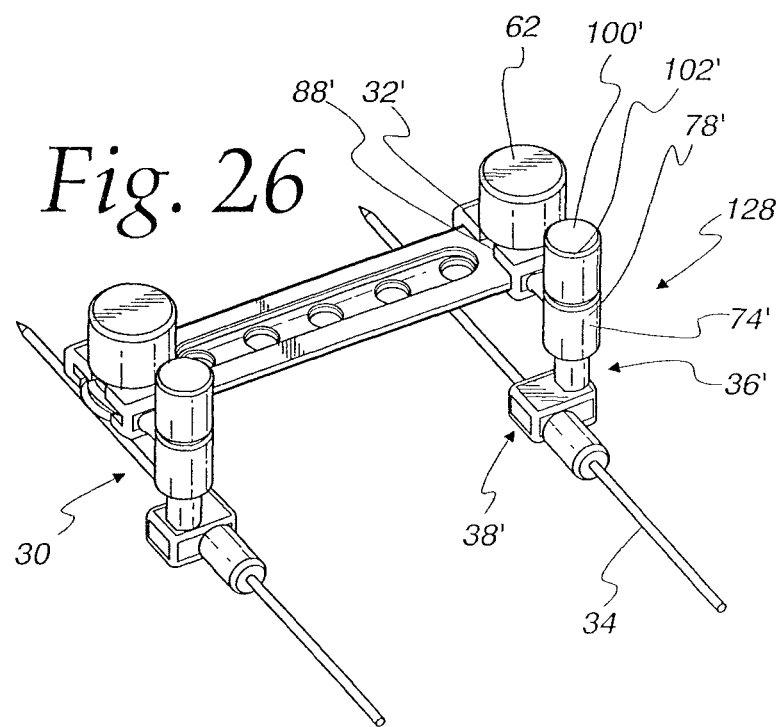
FIG. 26 is a perspective view of the components in FIGS. 23-25.

In this embodiment, the frame part 32 has a U-shaped slot/opening 88 through which one of the fasteners 62 extends. As seen in FIG. 15, a neck 90 of the fastener 62 is movable into and out of the slot/opening 88 whereby the frame part 32 can be advanced lengthwise to adjacent one end of the combined bone plate 22 and elongate plate 54, as shown in FIG. 16. With the fastener 62 extended through the frame part 32 as shown, the neck 90 thereon is guided within the slot/opening 88. At one extreme in the range of movement of the part 32—towards the left side in FIG. 16—the neck abuts the base 92 of the slot/opening 88.

The bone part moving assembly 30 is movable away from the FIG. 16 position to a position wherein the frame part 32 abuts the fastener 62 at the opposite end of the combined bone plate 22 and elongate plate 54.

The fixation element support 36 consists of an elongate body 94 that slides guidingly within the cylindrical body 78 in a line indicated by the double-headed arrow 95 in FIG. 18. The body 94 has a flat 96 thereon that engages a complementary flat (not shown) on the cylindrical body 78 to make a keyed connection and thereby prevent relative turning of the cylindrical body 78 and the body 94 about their common axis 98.

An adjusting component 100 rests against the top of the cylindrical body 78 and is threadably engaged with the body 94. The component 100 is turned in opposite directions to move the body 94 in opposite directions along the path indicated by the double-headed arrow 96 relative to the frame 74. It is not necessary to show the details of this structure, as this type of adjusting mechanism is well known and may take many different forms. An enlarged head 102 is provided to input the turning torque and is made to be readily graspable between the fingers of a user. Accordingly, by turning the head 102 in opposite directions, the body 94 can be selectively raised and lowered relative to the frame part 32, as shown in FIG. 18.

The lower region of the body 94 defines the fixation element mount 38 which accommodates a stepped diameter sleeve 104 for the fixation element 34, which in this embodiment is in the form of a fixation pin. With the fixation element 34 supported on the fixation element mount 38, the sharpened leading edge 106 of the fixation element 34 can be advanced progressively into the bone in the direction of the arrow 108. The fixation element 34 is thus directed into the bone without passing through the bone plate 22. Once the fixation element 34 is directed into the bone, that region of the bone moves together with the fixation element 34, the fixation element support 36, and the frame 74, including the part 32 that is guided in the controlled path along the length of the bone plate 22.

It should be mentioned that the use of only one fixation element/pin 34 is but one system configuration. For more rigid fixation, two or more fixation elements 34 may be accommodated that are directed into the bone in either parallel directions, or in non-parallel orientations for improved fixation.

The invention contemplates different variations of holding structure. As one example, a bone clamp on either side could clamp the part 32 to bone.

Figure 27:
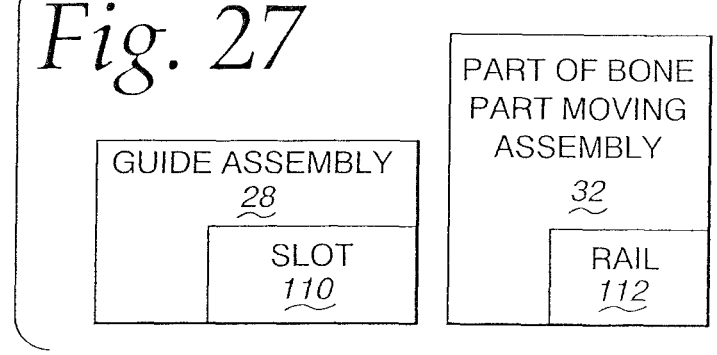
FIG. 27 is a schematic representation of alternative cooperating structure between the guide assembly and part of the bone part moving assembly, as shown schematically in FIG. 2.

Further, it should be noted that the formation of the guide rail on the guide assembly is one of different alternative constructions contemplated. For example, as shown in FIG. 27, the guide assembly 28 might define a slot 110 in which a rail 112 on the part 32 of the bone part moving assembly 30 moves. In other words, a reversal of elements would cause the cooperating structures to be guided in the same manner.

Still further, the generic showing of the guide structure is not limited to a basic rail and slot arrangement. One typical design would be a tongue-in-groove type connection of the part 32 to the track. In another variation, one or more pins, rails, or tracks extend from a connecting element on one side of the plate to capture the part 32 on the opposite side.

Figure 28:
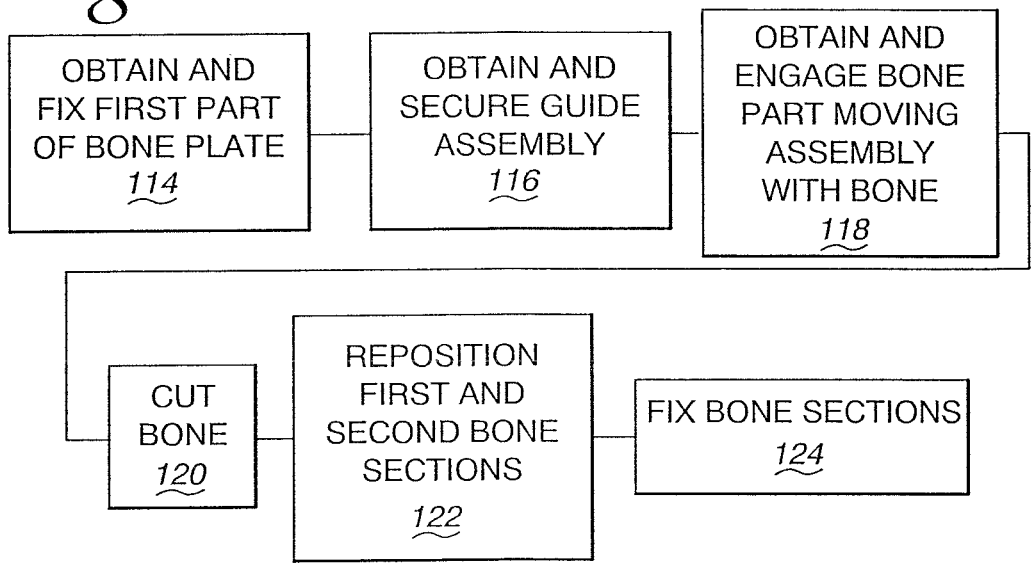
FIG. 28 is a flow diagram representation of a method of changing a configuration of a bone, according to the present invention.

With the above system, a method of changing a configuration of a bone having a length can be practiced, as shown in flow diagram form in FIG. 28. As shown at block 114, a bone plate having a length is obtained and a first part thereof is fixed to the bone at a first bone location.

As shown at block 116, a guide assembly is obtained and secured in an operative position in relationship to the bone.

As shown at block 118, a bone part moving assembly is obtained and is configured so that at least part of the bone part moving assembly cooperates with the guide assembly to be guided by the guide assembly in a controlled path. The bone part moving assembly is engaged with the bone at a second bone location spaced from the first bone location.

As shown at block 120, the bone is cut to define first and second bone sections and so that the bone part moving assembly engages the second bone section and the first bone location is on the first bone section.

As shown at block 122, the first and second bone sections are relatively repositioned into a desired relationship, thereby causing the part of the bone part moving assembly to move guidingly, together with the second bone section, in the controlled path.

As shown at block 124, the first and second bone sections are fixed in the desired relationship.

The guide assembly and bone part moving assembly are configured so that with the guide assembly in the operative position and the bone part moving assembly engaged with the bone at the second location, the first and second bone sections can be controllably relatively moved without requiring guided movement of any component, that is extended through the bone plate and into the bone, lengthwise of the bone plate.

More specifically, with reference to the embodiment herein described, and with initial reference to FIG. 16, the method is carried out by fixing a first part of the bone plate 22 at a first bone location through fixation structure at 126. The fixation structure 126 might be a fastener, clamp, etc., and is not limited in form.

The fixation element 34 on the bone part moving assembly 30 is engaged with the bone at a second bone location spaced from the first bone location.

After effecting cutting of the bone, the defined first and second bone sections are moved into a desired relationship, by lengthening, shortening, etc. As this occurs, the bone part moving assembly 30, together with the bone region engaged by the fixation element 34, follows guided movement of the bone part moving assembly part 32 in its controlled path as indicated by the double-headed arrow P (FIG. 16). The bone part moving assembly 30 may be directly manipulated as this repositioning is effected, or the bone portion penetrated by the fixation element 34 may be otherwise manipulated into the desired end position.

As noted above, the connection of the bone part moving assembly 32 to its respective bone region is effected without requiring that the fixation element 34, or any other component, be extended through the bone plate 22 and into bone.

Commonly, the fixation structure 126 will be in the form of the fasteners 24, that may be threaded to be advanced through the bone plate openings and strategically into the bone.

Once the fixation of the formed bone sections in the desired relationship is established and fixed, all of the components in FIG. 16 may be removed, leaving only the bone plate 22 in place, held by appropriate fixation structure.

The ability to reposition the fixation element support 36 and fixation element mount 38 thereon relative to the frame 74 allows the surgeon to select an optimal entry location for the fixation element 34 to effect the most stable connection of the bone part moving assembly 30. A range of potential entry locations is made possible by this construction.

In one form, the fixation structure 126 is made up of a bone attachment assembly 128, as shown in FIGS. 23-26. The bone attachment assembly 128 has essentially the same components and component function as the bone part moving assembly 30. The only significant difference in the depicted embodiment is that the bone attachment assembly 128 is a mirror image of the bone part moving assembly 30.

The parts of the bone attachment assembly 128 will now be identified with reference numerals corresponding to those identifying parts on the bone part moving assembly 30, but with a "'" designation added.

The bone attachment assembly 128 has a frame 74' with a cylindrical body 78' from which a part 32' projects. The frame 74' is slidably connected to a fixation element support 36' which has a fixation element mount 38' for a fixation element 34. An adjustable turning arrangement is provided with an adjusting component 100' to reposition the fixation element support 36' relative to the frame 74' and is operable through an enlarged head 102'. The part 32' has an elongate slot/opening 88' to accommodate the neck of the fastener 62 that extends therethrough.

While the bone attachment assembly 128 might be movable into different positions relative to the combined bone plate 22 and elongate plate 54, and fixed in those positions, in the embodiment shown, the bone attachment assembly 128 is fixed in a single position.

Each of the parts 32, 32' has an undercut 130, as shown for the part 32 in FIG. 17, which accepts a complementarily-shaped part of the respective fastener 62. By tightening a respective fastener 62, the parts 32, 32' can be fixed rigidly against movement lengthwise relative to the combined bone plate 22 and elongate plate 54.

With this configuration, either of the parts 32, 32' can be fixed relative to the combined bone plate 22 and elongate plate 54 while the other part 32, 32' can be movable along the length of the combined bone plate 22 and elongate plate 54. Thus, the surgeon has the option of sliding bone portions from either the left or the right depending upon which direction he/she would like the osteotomy cut.

Thus, by changing which of the parts 32, 32' is fixed, the bone part moving assembly 30 performs the function of the bone attachment assembly 128 and vice versa. For purposes of simplicity, a distinction is made throughout the drawings and in the Detailed Description between the bone part moving assembly 30 and bone attachment assembly 128 when in fact, as depicted, they are each, structurally and functionally, both a bone part moving assembly and bone attachment assembly, determined by which of the parts 32, 32' is fixed and which of the parts 32, 32' is allowed to guidingly move in use. Of course, those assemblies need not have the same construction.

The bone attachment assembly 128 is engaged with its respective bone region by selecting the desired entry location for the fixation element 34 and translating the same into the bone.

The bone part moving assembly 30 and bone attachment assembly 128 can be directly manipulated to effect movement of the respective bone portions. Alternatively, one or both of the bone portions can be otherwise manipulated (i.e., not directly through the bone part moving assembly 30 or bone attachment assembly 28).

The system provides a precise, controlled shortening without requiring a slotted bone screw hole in the plate. This results in a plate design that can be as short as needed and allows the amount of shortening to be as long as desired. The system allows the cut orientation to be made in whichever direction that the surgeon desires, and can be used with or without the placement of a lag screw. In addition, bone screws may be directed through the plate and into bone only a single time, and are not repetitively inserted, loosened, and re-tightened, resulting in more reliable thread purchase. Moreover, the system allows a design with or without utilization of an oblique lag screw across the osteotomy. The system also allows a design that can be used at the end of the bone. As a result, the plate length can be as short as desired, allows a uniform distribution of screw fixation, and allows use of a lag screw as an independent design option, while simplifying the procedure to only a limited number of steps. Moreover, since no slots need be present, the screw fixation can be placed close to both sides of the osteotomy site, improving fixation. In addition, the direction of the osteotomy cut can be offered in either direction at the preference of the surgeon, and it eliminates the need for asymmetric, lopsided plate configurations that exist with many current designs.

Figure 29:
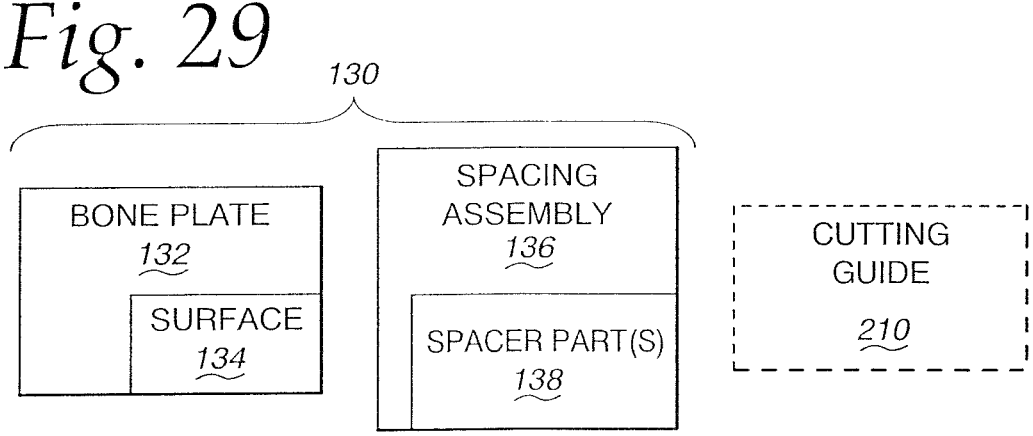
FIG. 29 is a schematic representation of a system for facilitating changing of a configuration of a bone, according to the invention, and consisting of a bone plate and a spacing assembly.

The invention is also directed to a system for facilitating changing of a configuration of a bone, as shown schematically at 130 in FIG. 29, The system 130 consists of a bone plate 132, which for purposes of the system 130 has a generic construction that can be the same as, or different than, the bone plate 22, described above. That is, the bone plate 132 may consist of a simple bone plate alone, such as the bone plate 22, or may be made up of a combination of components, such as the bone plate 22 and the guide assembly 28, as previously described. Regardless of its precise construction, the bone plate 132 has a surface 134 to overlie a bone surface to which the bone plate 132 is to be fixed in an operative position.

The system 130 further consists of a spacing assembly 136 configured to be placed together with the bone plate 132 selectively in: a) a cutting state wherein the spacing assembly 136 maintains a gap region between at least a part of the bone plate surface 134 and a bone surface which the bone plate surface 134 is situated to overlie; and b) a second state wherein the at least part of the bone plate 132 can be moved towards the surface of the bone to be closer to the surface of the bone than is possible with the bone plate 132 and spacing assembly 136 in the cutting state.

Accordingly, with the spacing assembly 136 and bone plate 132 in the cutting state, a cutting component can be directed fully through a bone into the gap region. The gap region allows travel of the cutting component thereinto a selected distance before the cutting component contacts either the bone plate 132 or any other part of the spacing assembly 136. While not so limited, the gap may be in the range of 2-4 millimeters, but could be less or considerably more. After the bone is cut, the bone plate 132 and spacing assembly 136 can be changed into the second state, whereupon the at least part of the bone plate 132 can be moved towards the bone surface, to be against or adjacent thereto, thereby allowing placement of the bone plate 132 into its operative position.

Once again, the schematic depiction of components in FIG. 29 is intended to encompass a wide range of variation of the basic components shown herein and their interaction. The specific forms described hereinbelow are exemplary in nature only.

Referring now to FIGS. 30-41, one preferred form of the system 130 will be described. In this embodiment, for purposes of simplicity, the depicted combined bone plate 22 and guide assembly 28 will be considered to make up the bone plate 132. The guide feature of the guide assembly 28 is not required to make the inventive system 130 operable, although it is utilized with the system 130 configured as in FIGS. 37-41.

The spacing assembly 136, in its most basic form, consists of at least one spacer part 138, as shown schematically in FIG. 29.

In the depicted embodiment, the spacing assembly 136 has a frame 140 with separate spacer parts 138a, 138b. The frame 140 has a generally flat wall 144 on which the cutting guide 142 is formed and from which the spacer parts 138a, 138b project in cantilever fashion. In this embodiment, the spacer parts 138a, 138b project orthogonally from the wall 144.

An arm 146 projects in cantilever fashion from the wall 144 approximately midway between the spacer parts 138a, 138b. In this embodiment, the arm 146 likewise projects orthogonally from the wall 144.

Each of the spacer parts 138a, 138b is formed as a flat wall 148a, 148b, respectively. The arm 146 is formed likewise as a flat wall 150.

In each of FIGS. 30-36, the spacing assembly 136 and bone plate 132 are shown in the aforementioned cutting state. In the cutting state, the spacer parts 138a, 138b reside between the bone plate 132 and a surface 152 of the bone 10. As a result, a gap region at 156 is maintained between the bone plate surface 134 and the bone surface 152 between the spacer parts 138a, 138b. The gap region thickness is dictated by the thickness t of each of the spacer parts 138a, 138b. Preferably, the thickness t for each of the spacer parts 138a, 138b is the same and on the order of 1-3 mm, whereby the gap thickness is substantially uniform over the full extent thereof between the spacer parts 138a, 138b.

The cutting guide 142 is configured so that the cutting component 158 on a cutting instrument 160 can be controllably guided through the bone 10 and the surface 152 thereon and into the gap region 156, thereby allowing complete unobstructed cutting of the bone 10 through the surface 152 that is under the bone plate 22.

The cutting guide 142 may be configured to guide the cutting component 158 and/or another part of the cutting instrument 160, Typically, the cutting component 158 will be a blade, and in this embodiment the blade will be guided selectively in any of slots 162a, 162b, 162c, 162d, 162e which are arranged in spaced, parallel relationship. Movement of the cutting component 158 in any of the slots 162 guides the cutting component 158 in a controlled path to an uppermost travel point that extends into the gap region 156 without contacting the bone plate 132.

The configuration of the frame 140 allows the spacer parts 138a, 138b to maintain the gap region 156 at spaced locations that, in addition to providing a potentially wide gap region, provide a stable mount for the cutting guide 142 and additionally stabilize the bone plate 132 as a procedure is performed, as described below.

The cantilevered arrangement of the spacer parts 138a, 138b and arm 146 with respect to the wall 144 facilitates changing of the spacing assembly 136 and bone plate 132 between their cutting and second states. More specifically, each of the spacer parts 138a, 138b has a bifurcated free end region. The bifurcation produces U-shaped slots 163a, 163b, respectively in the spacer parts 138a, 138b.

The arm 146 has a similar construction with a U-shaped slot 164 formed therein. The slots 163, 164 are elongate and lines bisecting the slots 162, 164 are substantially parallel.

Figure 34:
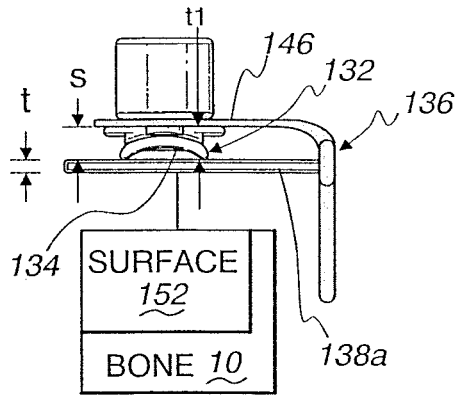
FIG. 34 is an end elevation view of the system in FIGS. 30-33.
Figure 35:
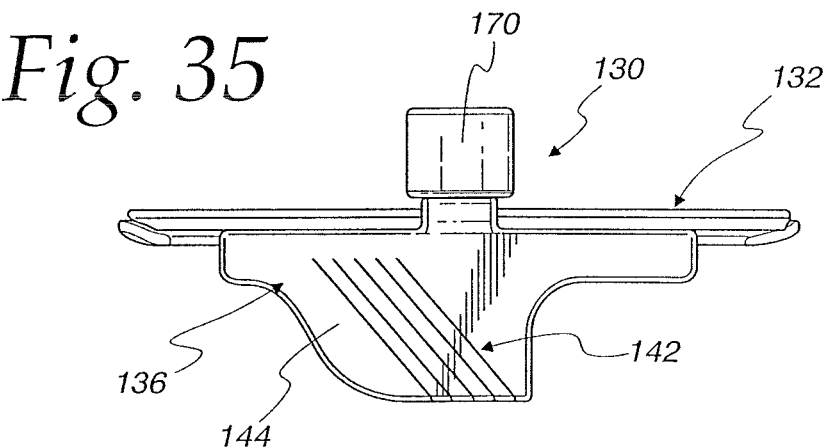
FIG. 35 is a side elevation view of the system in FIGS. 30-34.
Figure 36:
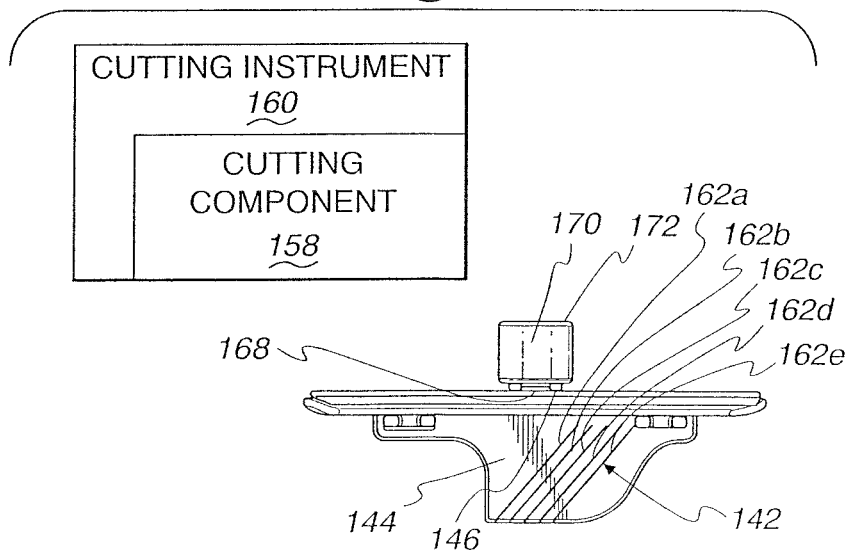
FIG. 36 is an elevation view from the side opposite that in FIG. 35.
Figure 37:
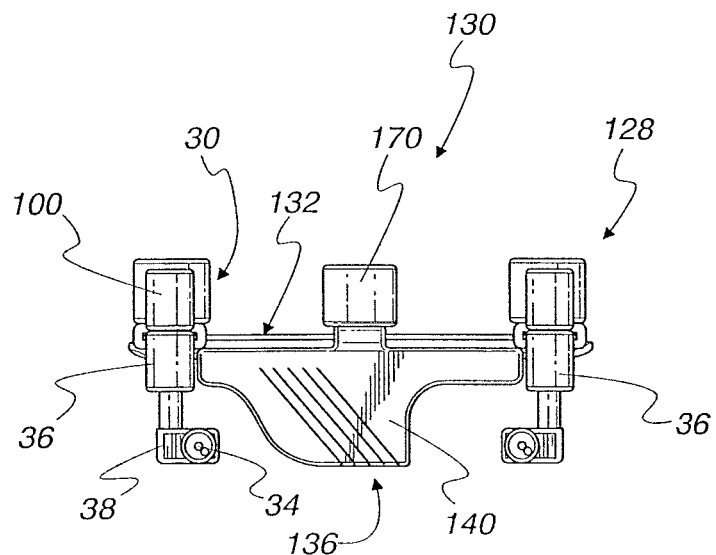
FIG. 37 is a view of the system as in FIG. 35 with bone part moving and fixation element support assemblies incorporated.
Figure 38:
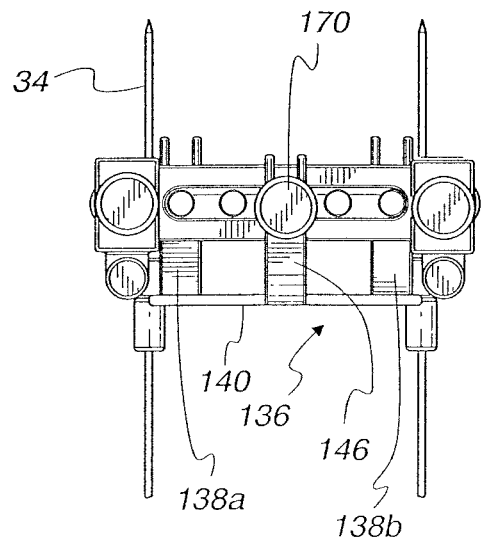
FIG. 38 is a plan view of the components in FIG. 37.
Figure 39:
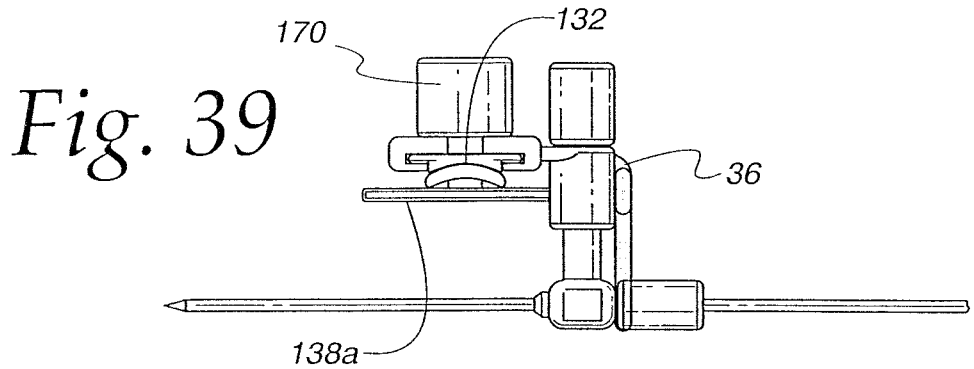
FIG. 39 is an end elevation view of the components in FIGS. 37 and 38.
Figure 40:
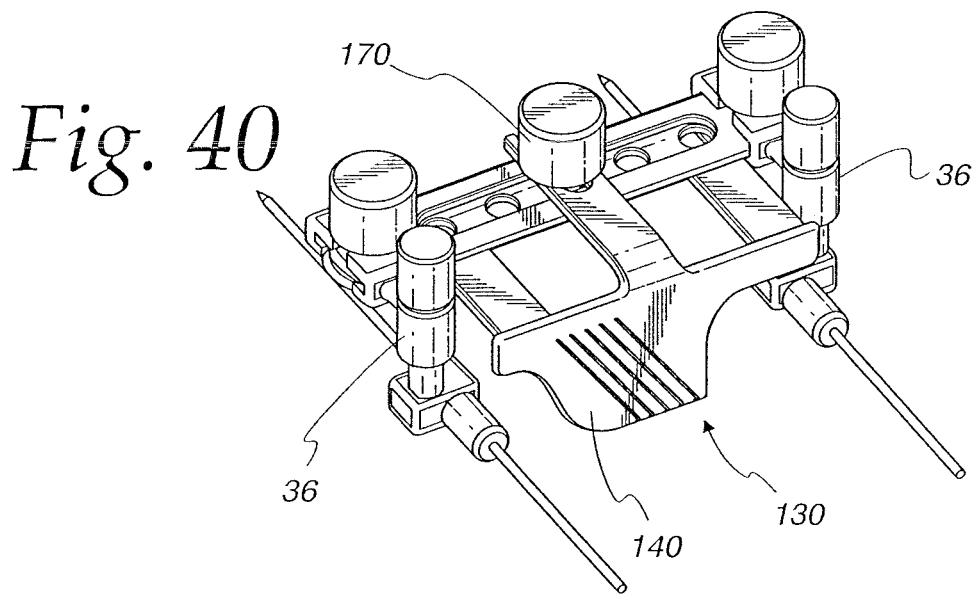
FIG. 40 is a perspective view of the components in FIGS. 37-39.
Figure 41:
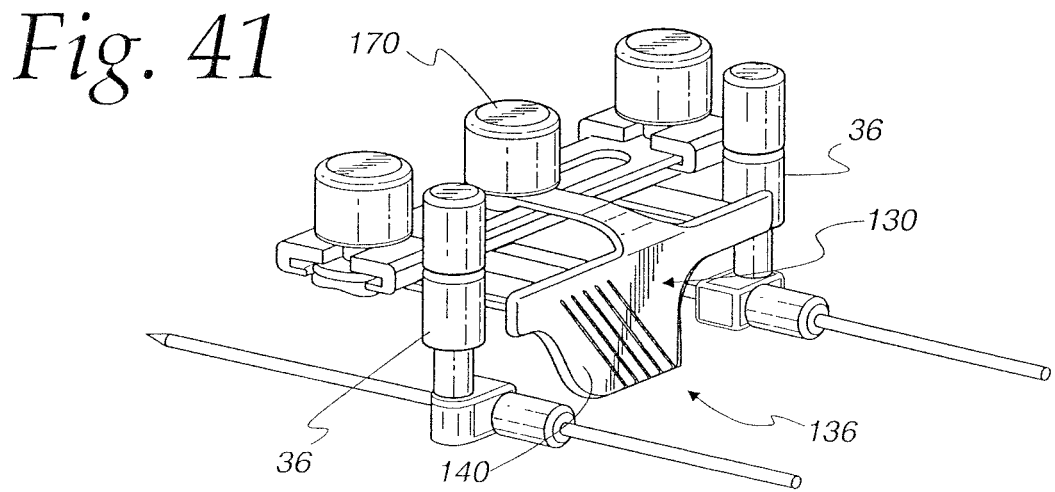
FIG. 41 is a view as in FIG. 40 but from a different perspective.

The arm 146 is spaced above the spacer parts 138a, 138b, from the FIG. 34 perspective. The spacing distance S between the arm 146 and spacer parts 138a, 138b is approximately equal to the effective thickness t1 of the bone plate 132. Accordingly, with the spacing assembly 136 and bone plate 132 in the cutting state, the bone plate 132 is sandwiched between the arm 146 and the spacer parts 138a, 138b. The bone plate 132 and spacing assembly 136 may be configured so that the frame 140 frictionally grips the bone plate 132 whereby the frame 140 and bone plate 132 might be pre-assembled and manipulated as a unit to initiate a procedure.

In this embodiment, with the spacing assembly 136 and bone plate 132 in their second state, the spacer assembly 136 is fully separated from the bone plate 132, as shown in dotted lines in FIG. 32. Changing of the spacing assembly 136 and bone plate 132 from the second state into the cutting state can be effected by translating the spacing assembly 136 from the dotted line position in the direction indicated by the arrow 166. This movement may be guided by a guide component 168, which in this case is defined by a reduced diameter neck on a fastener 170. The fastener 170 is threaded to be engaged with the bone plate 132 and has an enlarged head 172 configured to facilitate grasping between a user's fingers.

The slot 164 has a width slightly greater than the effective diameter of the guide component 168. Accordingly, the guide component 168 will guide movement of the spacing assembly 136 from its separated position towards the position it assumes with the spacing assembly 136 and bone plate 132 in their cutting state. Once the cutting state is achieved, the fastener 170, extending through the arm 146, can be tightened to the bone plate 132 to fix the position of the arm 146 relative to the bone plate 132.

Without other guide structure, the spacing assembly 136 can both slide and pivot relative to the fastener 170 around the fastener axis 174 in a path parallel to a reference plane.

Additional guiding of the spacing assembly 136 relative to the bone plate 132 can be accomplished through the spacer parts 138a, 138b. The spacer parts 138a, 138b are spaced from each other and the arm 146 so that the slots 162a, 162b each aligns with one of the through openings 52 on the bone plate 132 with the fastener 170 directed through the arm 146 and into the bone plate 132. Thus, with a typical threaded fastener 176 directed through each of the bone plate through openings 52 and the slots 162 and into the bone 10 without being tightened, projecting lengths on the fasteners 176 can be guided within the slots 162, whereby the spacing assembly 136 can be controllably guided in a substantially straight translatory path moving between the dotted line position in FIG. 32 to the solid line position therein.

The same fasteners 176 may be tightened by themselves, or in conjunction with the fastener 170, to secure the frame 140 positively relative to the bone plate 132 in preparation for cutting the bone 10.

It is also contemplated that the spacing assembly 136, the cutting guide 142, and bone plate 132 may be maintained operatively securely with respect to the bone 10, with the spacing assembly 136 and bone plate 132 in their cutting state, without requiring an extension of fasteners through the bone plate 132.

In one form, as shown in FIGS. 37-41, the aforementioned bone plate moving assembly 30 and fixation element support 36 may be incorporated, with the understanding that, as noted above, these assemblies have interchangeable structure and function.

As described above, the fixation element mount 38 is movable guidingly relative to the fixation element support 36, with this movement controlled through an adjusting mechanism operable through a threaded adjusting component 100. By turning the adjusting component 100, the fixation element 34 on the fixation element mount 38 is movable selectively towards and away from the bone plate 132.

With the fixation element 34 directed into a bone under the bone plate 132, the adjusting component 100 can be turned. By bracing against the fixation element 34, the bone plate 132 can be drawn towards the underlying bone surface to captively hold the frame 140 against the bone 10.

The bone attachment assembly 128 can be similarly used to generate a captive force upon the frame 140 at a location spaced lengthwise relative to the bone plate 132 from the bone part moving assembly 30.

Of course, the invention contemplates a more generic structure for producing this captive force, within the generic showing of FIG. 2. The depicted structure is exemplary in nature only.

The structures as described above represent exemplary forms of the invention and, as noted, are not to be viewed as limiting in nature. As noted above, within the generic showing of FIG. 29, it is contemplated that the spacing assembly 136 may have a dedicated function strictly to maintain the gap region between at least a part of the bone plate surface 134 and a bone surface which the bone plate surface 134 is situated to overlie while using any conventional cutting instrument and/or cutting guide. That is, the structure that guides the cutting instrument may be independent of the spacing assembly 136.

Additional preferred forms of the spacing assembly 136 are described hereinbelow with respect to FIGS. 42-51.

In FIGS. 42-46, a system is shown at 130" consisting of a spacing assembly 136" and the bone plate 22 shown without, but which might incorporate, a guide such as the rail 73, The bone plate 22 has the aforementioned surface 48 to overlie the surface 152 on the bone 10 with the bone plate 22 in its operative position, as shown in FIG. 47.

As noted above, the spacing assembly 136 might be a dedicated system usable in conjunction with a separate cutting guide, as shown schematically at 210 in FIG. 29. In this particular embodiment, a cutting guide 212, performing the function of the cutting guide 210, is integrated into the spacing assembly 136".

The spacing assembly 136" has separate spacer parts 138a", 138b" that reside between the bone plate 22 and the bone surface 152 with the spacing assembly 136" and bone plate 22 in the cutting state, as seen clearly in FIGS. 44 and 46, wherein the gap region 156" is maintained between at least a part of the bone plate surface 48 and the bone surface 152. In this form, the gap region 156" is maintained over the entire length of the bone plate surface 134.

In this embodiment, the spacing assembly 136" has a frame 140" that moves as one piece. The frame 140" defines at least a part of the cutting guide 212 and at least one of the spacer parts 138a", 138b". In this embodiment, the frame 140" defines both of the spacer parts 138a", 138b", that maintain the gap region 156" at spaced locations along the length of the bone 10.

The frame 140" has a wall 144" on which the cutting guide 212 is provided. At least one, and in this embodiment both, of the spacer parts 138a", 138b" project in cantilever fashion from the wall 144".

The frame 140" defines an arm 146" that projects from the wall 144". The bone plate 22 resides between the arm 146" and in this case both spacer parts 138a", 138b" with the bone plate 22 and spacing assembly 136" in the cutting state.

The spacing assembly 136" further includes an adjustable setting component 214 that is advanced through/from the arm 146" to against the bone plate 22 to thereby bear the bone plate 22 to against the spacer parts 138a", 138b" with the bone plate 22 and spacing assembly 136" in the cutting state so as to fix the relationship between the frame 140" and bone plate 22.

In the depicted embodiment, the arm 146" resides between the spacer parts 138a", 138b", in lengthwise relationship to the bone 10, as shown by the double-headed arrow L in FIG. 43. The location of the arm 146" is dictated by the arrangement of openings 52 in the bone plate 22, as explained below, and in this case is offset closer to the spacer part 138a".

In this embodiment, the adjustable setting component 214 has a threaded body 216 and a head 218 that can be engaged and manipulated to turn the body 216 around its axis 220 to advance or withdraw the body 216 in relationship to the bone plate 22.

In this embodiment, the head region is enlarged sufficiently to allow hand manipulation by grasping the head 218 between a user's fingers. A fitting 222 is also provided in the head 218 to allow turning with a tool 224 having a fitting 226 complementary to the fitting 222.

The adjustable setting component 214 and frame 140" can be made to cooperate with the bone plate 22 in different manners, as discussed below. As depicted, the body 216 is threaded through the centermost bone plate opening 52 whereby the relationship of the spacing assembly 136" and the bone plate 22 is established along its length and orthogonally to its length. As depicted, a threaded insert 229 is provided on the arm 146" and has spaced flanges 230, 231 between which the arm thickness is captive. With the threaded body 216 engaged with the plate 22 as shown in FIG. 44, the plate 22 becomes captive between the threads on the body 216 and the spacer parts 138a", 138b".

The cutting guide 212 is configured and functions in substantially the same manner as the cutting guide 142, described above, and has slots 162a", 162b", 162c", 162d", 162e", 162f" that cooperate with the cutting instrument 160, as previously described, to precisely control the cutting paths for the cutting component 158 as the bone 10 is cut.

The wall 144" has an integrally formed discrete tab 233 that projects in cantilever fashion on the wall 144" and is configured to be grasped between a user's fingers to facilitate handling of the spacing assembly 136".

In this embodiment, with the spacing assembly 136" initially fully separated from the bone plate 22, the threaded body 216 on the adjustable setting component 214 can be withdrawn sufficiently to allow the bone plate 22 to be placed between the arm 146" and spacer parts 138a", 138b".

The bone plate 22 can be aligned with the bone 10 and placed thereagainst in its desired end operative position before or after the spacing assembly 136" is engaged with the bone plate 22. A plurality of fasteners 176 are directed through preferably a plurality of the bone plate openings 52 to stabilize the bone plate 22 on each side of the cut location. Any of the openings 52 can be used so long as they do not interfere with the ultimate placement of the spacing assembly 136", as seen most clearly in FIG. 43.

If the bone plate 22 is placed in the operative position before being engaged with the spacing assembly 136", the fasteners 176 are tightened adequately to establish the lengthwise position of the bone plate 22 while allowing the bone plate 22 to be raised to allow the spacing assembly 136" to be translated from a starting spaced position, spaced from the bone plate 22, to a position underneath the bone plate as shown in FIG. 43. By then turning the adjustable setting component 214, the relationship between the spacing assembly 136" and bone plate 22 can be fixed, whereupon the fasteners 176 can be further tightened to cause the bone plate 22 to be urged towards the bone 10, thereby producing a captive holding force upon the spacer parts 138a", 138b" between the bone plate 22 and the bone 10.

The cutting of the bone 10 can then be carried out, after which the adjustable setting component 214 and fasteners 176 are loosened adequately that the spacing assembly 136", together with its associated cutting guide, can be separated from the bone plate 22 and bone 10.

The separate bone sections 14, 16 can then be moved relative to each other by removing the fasteners 176 on one of the bone sections 14, 16 and effecting relative movement through structure as described above, or any other structure known by those skilled in this art. The eventual tightening of all of the fasteners 176 completes the procedure to maintain the bone plate 22 fixed in its operative position.

The bone plate 22 and spacing assembly 136" may alternatively be engaged and either loosely held together or held together as a unitary mass by tightening the adjustable setting component 214 before the bone plate 22 is aligned over its operative position.

In another alternative form, the adjustable setting component 214 may bear against the plate without penetrating an opening 52 or by penetrating an opening 52 with or without threaded engagement therewith. A stepped, unthreaded outer diameter at the free end of the body 216 permits the latter.

In FIGS. 48-51, a further modified form of spacing assembly, according to the present invention, is shown at 136'''.

The spacing assembly 136''' may be an independent structure with a dedicated function that requires a separate cutting guide 210, as shown in FIG. 29. However, in this embodiment, the spacing assembly 136' integrates a cutting guide 212", substantially the same as the cutting guide 212 shown in the prior embodiment.

The spacing assembly 136''' has a frame 140" with spacer parts 234a, 234b, performing the function of the spacer parts 138a", 138b" in the prior embodiment. In this embodiment, the spacer parts 234a, 234b are threaded bodies 236a, 236b respectively on adjustable setting components 214a, 214b.

In this embodiment, the frame 140''' has a U-shaped portion 238 that overlies the bone plate 22 with the bone plate 22 and spacing assembly 136''' in the cutting state, as shown in each of FIGS. 48-51. The "U" shape is defined by spaced legs 240, 242 that are connected by a base portion/wall 244.

In this embodiment, the spacing assembly 136''' has at least one, and as depicted preferably two, setting components 214a, 214b having associated threaded bodies 236a, 236b, respectively. Each of the adjustable setting components 214a, 214b has the same construction, with the exemplary adjustable setting component 214a having a head 250a through which the body 236a is turned. The free end 252a of the body 236 has a non-sharp/flat shape with an area large enough that it can be borne against the bone surface 152 with a substantial force without appreciably penetrating the same.

With the legs 240, 242 overlying the bone plate 22, as shown in FIG. 49, threaded openings in inserts 229a''', 229b''' that receive the bodies 236a, 236b, align with bone plate openings 52 on opposite sides of the bone cut location. By manipulating the head 250a, the body 236a, which passes through the arm 240, can be advanced through one of the bone plate openings 52 to project past the bone plate surface 48, as seen most clearly in FIGS. 48 and 51. As a result, the free end surface 254a will keep the bone plate surface 48 from contacting the bone 10, thereby to maintain the gap region 156 at a desired dimension. The cooperation between the bodies 236a''', 236b''' and bone plate 22 may be the same as the cooperation between the bodies 236a, 236b and bone plate 22, as described above.

Thus, with both setting components 214a, 214b directed through their respective legs 240, 242 and the bone plate 22, the free end surface 254a on the setting component 214a and the free end surface 254b on the setting component 214b produce a bridged support for the region of the bone plate 22 therebetween where the bone cut is to be made.

The threaded bodies 236a, 236b, if threadably engaged with the bone plate 22, cause the bone plate 22 to be captive between the threads on the bodies 236a, 236b and the legs 240, 242. This creates a unitary mass that moves as one piece. Regardless of the precise cooperation between the bodies 236a, 236b and the bone plate 22, extending the surfaces 254a, 254b further beyond the bone plate 22 creates a greater dimension for the gap region 156.

As with the prior embodiment, fasteners 176 can be strategically placed before the spacing assembly 136''' is placed together with the bone plate 22 in the cutting state. Tightening of the fasteners 176 enhances the stabilization of the spacing assembly 136''' afforded by the projecting bodies 236a, 236b.

As in the prior embodiment, the head 250a may incorporate a fitting 256 to cooperate with a fitting 258 on a tool 260.

The configuration of the head 250a also facilitates a certain degree of hand tightening.

Leg extensions LE1, LE2 (FIG. 50) are provided to abut the plate 22, or another structure such as a guide (not shown), to block the spacing assembly 136''' against skewing relative to the plate 22.

The base portion/wall 244 on the frame 140''' has a discrete tab 228''' projecting from the base portion/wall 244 that is configured to be grasped between a user's fingers to facilitate handling of the spacing assembly 136'''.

The cutting guide 212''' functions in the same manner as the aforementioned cutting guide 212.

As depicted, the frame 140''' has a single piece that defines at least part, and as depicted all, of the legs 240, 242, the base portion/wall 244, the tab 228''', and the cutting guide 212'''.

In all embodiments, while not required, each of the cutting guide 212, 212''' projects in cantilever fashion from the associated frame 140", 140'''.

While the cutting guide are shown with multiple slots, cutting guides with virtually an unlimited number of different constructions are contemplated. For example, the cutting guide may have a single fixed slot, multiple fixed slots, a single slot that can be moved to guide the formation of spaced cuts, etc.

The spacing assembly 136''' and bone plate 22 can be placed in the cutting state in different manners. The spacing assembly 136''' may be preassembled to the bone plate 22 with the setting components extended or more preferably retracted so as not to extend beyond the bone plate surface 48. By then using fasteners 176 to locate the bone plate 22, the setting components 214a, 214b can be extended to the degree necessary to produce the desired dimension of the gap region 156. Coordinated tightening and loosening of the fasteners 176 and setting components 214a, 214b permits a desired gap dimension to be positively maintained.

Once cutting of the bone takes place, either using the cutting guide 212''' or another structure, the spacing assembly 136''' can be separated by loosening the setting components 214a, 214b, Once the setting components 214a, 214b are retracted, the bone plate 22 can be moved into its operative position. Until the spacing assembly 136''' is fully separated from the bone plate 22, it can be used to manipulate the bone plate 22 engaged by the frame 140''' conveniently through the tab 228'''.

With the structure as described above, a method of changing a configuration of a bone can be performed as shown in flow diagram form in FIG. 52.

As shown at block 290, a bone plate and spacing assembly are obtained.

As shown at block 292, the bone plate and spacing assembly are placed in the cutting state wherein: a) the bone plate is connected to the bone and overlies a surface of the bone; and b) the spacing assembly cooperates between the bone plate and bone so as to maintain a gap region between at least a part of the bone plate and the bone surface which the bone plate overlies.

As shown at block 294, a cutting component is obtained and used to cut through the bone up to and through the bone surface that the bone plate overlies to define first and second bone portions.

As shown at block 296, after cutting through the bone, the bone plate and spacing assembly are changed from the cutting state into a second state wherein the at least part of the bone plate can be moved towards the surface of the bone to be closer to the surface of the bone than is possible with the bone plate and spacing assembly in the cutting state.

To complete the procedure, as shown at block 298, the bone plate is moved towards the bone surface into its operative position preparatory to final fixation.

As noted above, each of the spacing assemblies may be made without an integral cutting guide. The structures absent a cutting guide may otherwise be the same as described herein. For example, as shown at FIG. 46, the cutting guide 212 might be eliminated by essentially removing that portion of the frame 140''' below the dotted line at 300.

In FIG. 53, a still further alternative embodiment is depicted wherein spacer parts $234a^{4'}$, $234b^{4'}$ make up a spacing assembly corresponding to the spacing assembly 136'. The spacer parts $234a^{4'}$, $234b^{4'}$ are threaded into and through the plate 22 whereby the free end surfaces $254a^{4'}$, $254b^{4'}$, respectively thereon, are abuttable to the bone surface 152 to maintain the cutting gap. This cutting gap has a dimension dictated by the degree of downward projection of the free end surfaces $254a^{4'}$, $254b^{4'}$ in FIG. 53 below the plate surface 48. The spaced locations of the spacer parts $234a^{4'}$, $234b^{4'}$ cause the plate 22 to be stably supported over the bone surface 152 between the spacer parts $234a^{4'}$, $234b^{4'}$.

The cutting guide $212^{4'}$, as depicted, is otherwise similar in construction to the spacing assembly 136'''. That is, the depicted cutting guide $212^{4'}$ has a frame $140^{4'}$ that differs in construction from the frame 140''' by eliminating the portions penetrated by the spacer parts 234a, 234b to form truncated ends E1, E2. Accordingly, the cutting guide frame $140^{4'}$ must be held in place by separate structure, in this case a threaded fastener 310 that extends through the frame $140^{4'}$ and into the plate 22.

Further, in this embodiment, as in all embodiments herein, it is contemplated that the cutting guide might be connected by an alternative structure. For example, as shown in FIG. 54, a generic form of cutting guide 312, encompassing all forms herein, and others, might be held in place on a generic form of plate 314, encompassing all forms herein, and others, through one or more connectors 316, 318, respectively on the cutting guide 312 and plate 314, that cooperate to maintain a desired operative relationship between the cutting guide 312 and plate 314 during a procedure. These connectors 316, 318 may take any form, as generally depicted, for example a clip arrangement, etc.

The foregoing disclosure of specific embodiments is intended to be illustrative of the broad concepts comprehended by the invention.

The invention claimed is:

1. A method of changing a configuration of a bone having a length, the method comprising the steps of:
   obtaining a bone plate;
   obtaining a spacing assembly;
   placing the bone plate and spacing assembly in a cutting state wherein: a) the bone plate is connected to the bone and overlies a surface of the bone; and b) the spacing assembly cooperates between the bone plate and bone so as to maintain a gap region between at least a part of the bone plate and the bone surface which the bone plate overlies;
   obtaining a cutting instrument with a cutting component;
   with the bone plate and spacing assembly in the cutting state, using the cutting component on the cutting instrument to cut into the bone towards the gap region and at least substantially through the bone between first and second bone portions;
   after cutting into the bone, changing the bone plate and spacing assembly from the cutting state into a second state wherein the at least part of the bone plate can be moved towards the surface of the bone to be closer to the surface of the bone than is possible with the bone plate and spacing assembly in the cutting state.

2. The method of changing a configuration of a bone according to claim 1 further comprising the step of moving the at least part of the bone plate towards the bone surface after cutting into the bone to thereby place the bone plate in an operative position on the bone.

3. The method of changing a configuration of a bone according to claim 2 further comprising the step of securing the bone plate in the operative position with the bone plate spanning the first and second bone portions.

4. The method of changing a configuration of a bone according to claim 3 wherein the bone plate has at least one through opening and at least one fastener is directed through the at least one through opening and into the bone, and the step of securing the bone plate comprises tightening the at least one fastener.

5. The method of changing a configuration of a bone according to claim 1 wherein with the bone plate and spacing assembly in the cutting state, using a cutting guide that is configured to guide movement of the cutting instrument and/or the cutting component on the cutting instrument in at least one controlled path to thereby strategically cut into the bone between the first and second bone sections.

6. The method of changing a configuration of a bone according to claim 5 wherein the cutting guide has a first elongate slot to guide movement of the cutting instrument and/or the cutting component in the one controlled path.

7. The method of changing a configuration of a bone according to claim 6 wherein the cutting guide has a second elongate slot to guide movement of the cutting instrument and/or the cutting component in a second controlled path.

8. The method of changing a configuration of a bone according to claim 6 wherein the spacing assembly is configured to maintain the gap region through spacer parts that act between the bone and bone plate at first and second spaced locations, the spacing assembly comprises a frame that moves as one piece and the frame comprises the spacer parts and the cutting guide.

9. The method of changing a configuration of a bone according to claim 8 wherein the frame comprises one piece that defines the spacer parts and at least a part of the cutting guide.

10. The method of changing a configuration of a bone according to claim 9 wherein the step of changing the bone plate and spacing assembly from the cutting state into the second state comprises translating the frame relative to the bone plate from a starting position spaced from the bone plate into an operative position.

11. The method of changing a configuration of a bone according to claim 8 further comprising the step of releasably fixing the frame relative to the bone plate to thereby maintain the bone plate and spacing assembly in the cutting state.

12. The method of changing a configuration of a bone according to claim 11 wherein the step of releasably fixing the frame comprises directing a fastener relative to the frame and into the bone plate.

13. The method of changing a configuration of a bone according to claim 11 further comprising the step of urging the bone plate towards the bone surface with the bone plate and spacing assembly in the cutting state before cutting through the bone.

14. The method of changing a configuration of a bone according to claim 13 wherein the step of urging the bone plate towards the bone surface comprises exerting a force on the bone plate at two spaced locations between which the bone is cut.

15. The method of changing a configuration of a bone according to claim 14 wherein the force is exerted at each of the two spaced locations through a fastener extending through the bone plate and into the bone.

16. The method of changing a configuration of a bone according to claim 14 wherein the step of urging the bone plate towards the bone surface causes a part of the spacing assembly to be compressibly captively held between the bone plate and the bone surface.

17. The method of changing a configuration of a bone according to claim 5 wherein the cutting guide is separate from a part of the spacing assembly.

18. The method of changing a configuration of a bone according to claim 1 wherein the spacing assembly is configured to maintain the gap region through spacer parts that act between the bone and bone plate at first and second spaced locations.

19. The method of changing a configuration of a bone according to claim 18 wherein the bone plate has a length, the first and second locations are spaced lengthwise of the bone plate and the bone is cut at a location between the first and second locations.

20. The method of changing a configuration of a bone according to claim 1 further comprising the step of captively engaging the bone plate between spaced surfaces on the spacing assembly.

21. The method of changing a configuration of a bone according to claim 1 wherein the bone plate has a length and with the bone plate and spacing assembly in the cutting state the gap region is defined over substantially an entire bone plate length.

22. The method of changing a configuration of a bone according to claim 1 wherein the gap region has a dimension of 1-3 mm between the bone plate and bone surface.

23. The method of changing a configuration of a bone according to claim 1 wherein the spacing assembly comprises a frame and at least one setting component with a free end, and the step of placing the bone plate and spacing assembly in the cutting state comprises advancing the at least one setting component relative to the frame and bone plate so as to bear the free end of the at least one setting component against the bone surface without appreciably penetrating the bone surface to thereby maintain at least a part of the gap region.

24. The method of changing a configuration of a bone according to claim 1 wherein the step of changing the bone plate and spacing assembly from the cutting state into the second state comprises separating at least a part of the spacing assembly from the bone and the bone plate.

25. The method of changing a configuration of a bone according to claim 1 wherein with the bone plate and spacing assembly in the cutting state, at least a part of the bone plate directly overlies the bone surface.

* * * * *